(12) United States Patent
Miwa

(10) Patent No.: US 8,232,099 B2
(45) Date of Patent: Jul. 31, 2012

(54) METHOD FOR TRANSCRIPTION/DEGRADATION DUAL CONTROL OF PROTEIN BY ANTIBIOTIC

(75) Inventor: Yoshihiro Miwa, Ibaraki (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 12/531,110

(22) PCT Filed: Mar. 14, 2008

(86) PCT No.: PCT/JP2008/055200
§ 371 (c)(1),
(2), (4) Date: Dec. 7, 2009

(87) PCT Pub. No.: WO2008/114856
PCT Pub. Date: Sep. 25, 2008

(65) Prior Publication Data
US 2010/0136654 A1 Jun. 3, 2010

(30) Foreign Application Priority Data
Mar. 14, 2007 (JP) ................................ 2007-065415

(51) Int. Cl.
*C12N 15/63* (2006.01)
*C12N 15/85* (2006.01)
*G01N 33/00* (2006.01)

(52) U.S. Cl. ...................... 435/320.1; 435/325; 435/455; 800/3

(58) Field of Classification Search .......................... None
See application file for complete search history.

(56) References Cited

U.S. PATENT DOCUMENTS

| 5,654,168 | A | 8/1997 | Bujard et al. ................ 435/69.1 |
| 2002/0007051 | A1 | 1/2002 | Cheo et al. ................... 536/23.1 |
| 2003/0208783 | A1 | 11/2003 | Hillen et al. ...................... 800/8 |
| 2009/0130763 | A1 | 5/2009 | Miwa ............................ 435/471 |

FOREIGN PATENT DOCUMENTS

| EP | 1935978 | 6/2008 |
| JP | 11-506901 | 6/1999 |
| JP | 2003-515314 | 5/2003 |
| JP | 2004-500061 | 1/2004 |
| WO | WO 2007/032555 | 3/2007 |
| WO | WO 2008/114856 | 9/2009 |

OTHER PUBLICATIONS (Glossary entry for "Repressor protein" in Lewin, B. Genes V. Oxford: Oxford University Press, 1995, p. 1252.).*
Wissmann et al (The EMBO Journal, vol. 10, No. 13, pp. 4145-4152, 1991).*
Verma et al (Nature, vol. 389, pp. 239-242, 1997;).*
Palu et al (J. Biotechnol. vol. 68, pp. 1-13, 1999).*
Luo et al (Nature Biotechnology, vol. 18, pp. 33-37, 2000).*
Verma and Weitzman, Gene Therapy: Twenty-first century medicine. Annual Review of Biochemistry, vol. 74, pp. 711-738, 2005.*
Edelstein et al, J. Gene Med. vol. 6, pp. 597-602, 2004.*
By Lai et al (The Journal of Gene Medicine, vol. 6, pp. 1403-1413, Nov. 2004).*
Matzke et al., "Tetracycline operator/repressor system to visualize fluorescence-tagged T-DNAs in interphase nuclei of *Arabidopsis*," Plant Mol. Biol. Rep., 2003, 21: 9-19.
Banaszynski et al., "A Rapid, Reversible, and Tunable Method to Regulate Protein Function in Living Cells Using Synthetic Small Molecules", Cell, 126(5): 995-1004 (2006).
Gossen et al., "Transcriptional Activation by Tetracyclines in Mammalian Cells", Science, 268(5218): 1766-1769 (1995).
Stankunas et al., "Conditional Protein Alleles Using Knockin Mice and a Chemical Inducer of Dimerization", Mol. Cell, 12(6): 1615-1624 (2003).
Yoshihiro Miwa et al., "Fluorescent Molecular Imaging in Living Mice", The Institute of Electrical Engineers of Japan Kenkyukai Shiryo, vol. BMS-07-3, No. 1-6, pp. 9-12 (2007) with English translation.
Yuri Yoshida et al., "Tet Niju Seigyokei ni yoru conditional gene targeting Gijutsu no Kaihatsu", BMB 2007 (Dai 30 Dai Annual Meeting of the Molecular Biology Society of Japan Dai 80 Kai The Japanese Biochemical Society Godo Taikai) Koen Yoshishu, Nov. 25, 2007, 4P-1311 with English translation.
International Search Report (PCT/JP2008/055200), dated Jul. 1, 2008.

* cited by examiner

*Primary Examiner* — Celine Qian
(74) *Attorney, Agent, or Firm* — Morgan, Lewis & Bockius LLP

(57) ABSTRACT

The present invention provides an expression vector, containing expressibly (a) a polynucleotide encoding a fusion protein of a mutant of a repressor protein, which binds to an antibiotic, and a target protein, and (b) a polynucleotide encoding a protein controlling the transcription of the polynucleotide in (a), the transcription of the polynucleotide in (a) and the degradation of said fusion protein, which is the expression product of the polynucleotide in (a), being controlled inside a cell by the presence or absence of an antibiotic inside the cell.

15 Claims, 16 Drawing Sheets

(A)

(B) wt-tetR / mut-tetR
 174
 7

(C) +MG132
 80
 41

(D) +Dox
 163
 140

(A)

(B)

SEQUENCE LISTING

<160> NUMBER OF SEQ ID NOS: 4

<210> SEQ ID NO 1
<211> LENGTH: 624
<212> TYPE: DNA
<213> ORGANISM: Serratia marcescens

<400> SEQUENCE: 1

```
atgtctagat tagataaaag taaagtgatt aacagcgcat tagagctgct taatgaggtc      60
ggaatcgaag gtttaacaac ccgtaaactc gcccagaagc taggtgtaga gcagcctaca     120
ttgtattggc atgtaaaaaa taagcgggct ttgctcgacg ccttagccat tgagatgtta     180
gataggcacc atactcactt tgccccttta aagggggaaa gctggcaaga ttttttacgt     240
aataacgcta aagttttag atgtgcttta ctaagtcatc gcgatggagc aaaagtacat      300
ttaggtacac ggcctacaga aaacagtat gaaactctcg aaaatcaatt agccttttta      360
tgccaacaag ttttttcact agagaatgca ttatatgcac tcagcgctgt ggggcatttt     420
actttaggtt gcgtattgga agatcaagag catcaagtcg ctaaagaaga agggaaaca      480
cctactactg atagtatgcc gccattatta cgacaagcta tcgaattatt tgatcaccaa     540
ggtgcagagc cagccttctt attcggcctt gaattgatca tatgcggatt agaaaaacaa     600
cttaaatgtg aaagtgggtc ttaa                                            624
```

<210> SEQ ID NO 2
<211> LENGTH: 207
<212> TYPE: PRT
<213> ORGANISM: Serratia marcescens

<400> SEQUENCE: 2

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 3
<211> LENGTH: 1035
<212> TYPE: DNA
<213> ORGANISM: Artificial
<220> FEATURE:
<223> OTHER INFORMATION: Synthetic hCre

<400> SEQUENCE: 3

```
atggtgtcca acctgctgac cgtgcatcag aacctgcccg ccctgcccgt ggacgccacc      60
tccgacgagg tgcgcaagaa cctgatggat atgttccgcg accgccaggc cttctccgag     120
cacacctgga agatgctgct gtccgtgtgc cgctcctggg ccgcctggtg caagctgaac     180
aaccgcaagt ggttccccgc cgagcccgag acgtgcgcg actacctgct gtatctgcag      240
gccagaggcc tggccgtgaa gaccatccag cagcacctgg ccagctgaa catgctgcac      300
cgccgctccg gcctgccccg cccctccgac tccaacgccg tgtccctggt gatgcgccgc     360
atccgcaagg agaacgtgga cgccggcgag gcgccaagc aggccctggc cttcgagcgc      420
accgacttcg accaggtgcg ctccctgatg gagaactccg accgctgcca ggacatccgc     480
aacctggcct ttctaggcat cgcctacaac accctgctgc gcatcgccga gatcgcccgc     540
atccgcgtga aggacatctc ccgcaccgac ggcggacgca tgctgatcca tcggccgc      600
accaagaccc tggtgtccac cgccggcgtg agaaggcccc tgtccctggg cgtgaccaag     660
ctggtggagc gctggatctc cgtgtccggc gtggccgacg accccaacaa ctacctgttc     720
tgccgcgtgc gcaagaacgg cgtggccgcc cctccgcca cctcccagct gtccaccgc      780
gctctagagg gcatcttcga ggccacccac cgcctgatct acggcgccaa ggacgactcc     840
ggccagcgct acctggcctg gtccggccac tccgcccgcg tggcgccgc ccgcgacatg      900
gcccgcgccg cgtgtccat ccccgagatc atgcaggccg cggctggac caacgtgaac      960
atcgtgatga actacatccg caacctggac tccgagaccg cgctatggt gcgcctgctg     1020
gaggacggcg actag                                                    1035
```

<210> SEQ ID NO 4
<211> LENGTH: 344
<212> TYPE: PRT
<213> ORGANISM: phage lambda

<400> SEQUENCE: 4

```
Met Val Ser Asn Leu Leu Thr Val His Gln Asn Leu Pro Ala Leu Pro
1               5                   10                  15

Val Asp Ala Thr Ser Asp Glu Val Arg Lys Asn Leu Met Asp Met Phe
            20                  25                  30

Arg Asp Arg Gln Ala Phe Ser Glu His Thr Trp Lys Met Leu Leu Ser
        35                  40                  45

Val Cys Arg Ser Trp Ala Ala Trp Cys Lys Leu Asn Asn Arg Lys Trp
    50                  55                  60

Phe Pro Ala Glu Pro Glu Asp Val Arg Asp Tyr Leu Leu Tyr Leu Gln
65                  70                  75                  80

Ala Arg Gly Leu Ala Val Lys Thr Ile Gln Gln His Leu Gly Gln Leu
                85                  90                  95

Asn Met Leu His Arg Arg Ser Gly Leu Pro Arg Pro Ser Asp Ser Asn
            100                 105                 110

Ala Val Ser Leu Val Met Arg Arg Ile Arg Lys Glu Asn Val Asp Ala
        115                 120                 125

Gly Glu Arg Ala Lys Gln Ala Leu Ala Phe Glu Arg Thr Asp Phe Asp
```

-continued

```
              130                 135                 140
Gln Val Arg Ser Leu Met Glu Asn Ser Asp Arg Cys Gln Asp Ile Arg
145                 150                 155                 160

Asn Leu Ala Phe Leu Gly Ile Ala Tyr Asn Thr Leu Leu Arg Ile Ala
                165                 170                 175

Glu Ile Ala Arg Ile Arg Val Lys Asp Ile Ser Arg Thr Asp Gly Gly
                180                 185                 190

Arg Met Leu Ile His Ile Gly Arg Thr Lys Thr Leu Val Ser Thr Ala
                195                 200                 205

Gly Val Glu Lys Ala Leu Ser Leu Gly Val Thr Lys Leu Val Glu Arg
    210                 215                 220

Trp Ile Ser Val Ser Gly Val Ala Asp Asp Pro Asn Asn Tyr Leu Phe
225                 230                 235                 240

Cys Arg Val Arg Lys Asn Gly Val Ala Ala Pro Ser Ala Thr Ser Gln
                245                 250                 255

Leu Ser Thr Arg Ala Leu Glu Gly Ile Phe Glu Ala Thr His Arg Leu
                260                 265                 270

Ile Tyr Gly Ala Lys Asp Asp Ser Gly Gln Arg Tyr Leu Ala Trp Ser
                275                 280                 285

Gly His Ser Ala Arg Val Gly Ala Ala Arg Asp Met Ala Arg Ala Gly
    290                 295                 300

Val Ser Ile Pro Glu Ile Met Gln Ala Gly Gly Trp Thr Asn Val Asn
305                 310                 315                 320

Ile Val Met Asn Tyr Ile Arg Asn Leu Asp Ser Glu Thr Gly Ala Met
                325                 330                 335

Val Arg Leu Leu Glu Asp Gly Asp
                340
```

METHOD FOR TRANSCRIPTION/DEGRADATION DUAL CONTROL OF PROTEIN BY ANTIBIOTIC

This application is a U.S. National Phase Application of International Application Number PCT/JP2008/055200 filed Mar. 14, 2008, which claims the benefit of Japanese Patent Application No. 2007-065415, filed Mar. 14, 2007, each of which is incorporated by reference in its entirety.

TECHNICAL FIELD

The present invention relates to a gene transcription control method and/or protein degradation control method by an antibiotic. In particular, the present invention relates to a dual control method including gene transcription control and protein degradation control by an antibiotic.

A computer readable text file, entitled "65393-5025-SeqListing.txt," created on or about Sep. 14, 2009 having a size of about 8 kb contains the sequence listing for this application and is hereby incorporated by reference.

BACKGROUND ART

Developments of gene expression systems that are controllable by external stimuli are attempted with the purpose of functional analyses or the like, of cellular proteins.

Japanese National-phase PCT Laid-Open Patent Publication No. 11-506901 discloses a transcription activator and a transcription inhibitor fusion protein that can control the expression of a gene linked to one or more tet operators. It is reported that, according to the transcription activator disclosed in Japanese National-phase PCT Laid-Open Patent Publication No. 11-506901, a control is possible in such a way that when tetracycline is present, the fusion protein binds a tet operator and transcription of the gene linked to the tet operator is stimulated, while in the absence of tetracycline, there is no binding or the like (therefore, there is no stimulation of transcription).

STANKUNAS K et al., "Conditional protein alleles using knockin mice and a chemical inducer of dimerization", Mol. Cell., 2003, Vol. 12, No. 6, p. 1615-24 discloses the fusion protein GSK-3β FRB* of an 89 amino acid domain FRB*, which is the smallest region of FRAP (i.e., FKBP12-rapamycin binding protein) required for FKBP-12 rapamycin binding, and GSK-3β (i.e., endogenous glycogen synthase kinase-3β). STANKUNAS K et al state that FRB* triggers destabilization of GSK-3β, in other words, GSK-3β is destabilized by fusion with FRB* and degraded. In addition, STANKUNAS K et al describe that GSK-3β FRB* binds to FKBP12 in the presence of a rapamycin derivative (C20-MaRap), and that this interaction stabilizes GSK-3β FRB*. The system by STANKUNAS K et al is described as one that promotes dimerization between FKB* and FKBP12 by the sole use of a rapamycin derivative.

DISCLOSURE OF THE INVENTION

The system described by STANKUNAS K et al requires four elements: (i) target protein (Target), (ii) FRB*, (iii) FKBP12 and (iv) rapamycin derivative (C20-MaRap). That is, the dimerization system by STANKUNAS K et al requires the presence of FKBP12, which is originally present inside the cell, as an element that stabilizes the GSK-3β FRB* fusion protein. Since the degradation control is effected only when an exogenous fusion protein and an intracellular normal protein are bound, an experiment must be conducted while taking into consideration possible detrimental effects to the cell when using the system described by STANKUNAS K et al. In addition, there has been no instance of clinical use for the rapamycin derivative used in STANKUNAS K et al, and further, there are many unknowns about how a superfluous effect such as an immune control effect affects an organism, and also needs for handling precautions with regard to waste after an experiment.

Consequently, there is a need for an alternative system or a system that is easier to use to control the amount of protein in a living cell using an artificial degradation control mechanism.

On the other hand, from the findings of the present inventors, it has been known that effectiveness of control is insufficient on the amount of protein expressed in a living cell in a system for gene transcription control such as that described in Japanese National-phase PCT Laid-Open Patent Publication No. 11-506901, as well as in a system for protein degradation control such as that described in STANKUNAS K et al. In such cases, due to insufficient suppression of the expression of an introduced gene when no induction is expected, introduction of genes exhibiting cytotoxicity, genes affecting cell multiplication and the like, is extremely difficult, and an accurate determination of the effects of the gene expression is difficult.

Consequently, there is a need for a system for further ensuring protein expression control inside a living cell.

Thus, the present invention provides, as described below, an expression vector for protein expression control of a target protein, a host cell or a host organism into which the expression vector has been introduced, a composition and a kit containing the expression vector, an expression control system, and an expression control method.

(1) An expression vector, containing expressibly
 (a) a polynucleotide encoding a fusion protein of a mutant of a repressor protein, which binds to an antibiotic, and a target protein, and
 (b) a polynucleotide encoding a protein controlling the transcription of the polynucleotide of (a),
 the transcription of the polynucleotide of (a) and the degradation of the fusion protein, which is the expression product of the polynucleotide of (a), being controlled inside the cell by the presence or absence of an antibiotic inside the cell.

(2) The expression vector according to (1) above, in which the polynucleotide of (b) encodes a protein that binds to the transcription control region of the polynucleotide of (a) and enhances the transcription of the polynucleotide, the protein being able to bind to the transcription control region only when bound to the antibiotic.

(3) The expression vector according to (1) or (2) above, in which the fusion protein that is the expression product of the polynucleotide in (a) is degraded inside the cell when not bound to the antibiotic.

(4) The expression vector according to any of (1) to (3) above, in which the antibiotic is a tetracycline-type antibiotic.

(5) The expression vector according to (4) above, in which the tetracycline-type antibiotic is tetracycline or its derivative selected from doxycycline, oxytetracycline, chlortetracycline or anhydrotetracycline.

(6) The expression vector according to any of (1) to (5) above, in which the mutant of the repressor protein is a mutant TetR protein.

(7) The expression vector according to (6) above, in which the mutant TetR protein has an amino acid sequence with at least one amino acid residue substituted in the amino acid sequence of the wild-type TetR protein.

(8) The expression vector according to (7) above, in which the substitution of amino acid residue exists at least any two sites among the aspartic acid at position 95, the leucine at position 101 and the glycine at position 102, in the amino acid sequence of the wild-type TetR protein.
(9) The expression vector according to any of (1) to (8) above, in which the target protein is a fluorescent protein or a luminescent protein.
(10) The expression vector according to any of (1) to (9) above, in which the target protein is a therapeutic protein.
(11) The expression vector according to any of (1) to (9) above, in which the target protein is a protein to be subjected to functional analysis.
(12) A host cell or a host organism transfected with the expression vector according to any of (1) to (11) above.
(13) A composition for intracellular or in vivo imaging containing the expression vector according to (9) above.
(14) A composition for therapeutic use containing the expression vector according to (10) above.
(15) A composition for use in protein functional analysis containing the expression vector according to (11) above.
(16) A composition according to any of (13) to (15) above used in combination with a tetracycline-type antibiotic.
(17) The composition according to (16) above, in which the tetracycline-type antibiotic is tetracycline or its derivative selected from doxycycline, oxytetracycline, chlortetracycline or anhydrotetracycline.
(18) A kit containing the expression vector according to any of (1) to (11) above, the host cell or the host organism according to (10) above or the composition according to any of (11) to (15) above.
(19) A protein expression control system for controlling the expression of a target protein inside a cell at the transcription level and the protein degradation level, containing
    a cell,
    an expression vector according to any of (1) to (11) above to be introduced into the interior of the above cell, and
    an antibiotic to be introduced into the interior of the above cell.
(20) A protein expression control system for controlling the expression of a target protein inside a cell at the transcription level and the protein degradation level, containing
    (a) a first expression vector containing expressibly a polynucleotide encoding a fusion protein of a mutant of a repressor protein, which binds to a an antibiotic, and a target protein, and
    (b) a second expression vector containing expressibly a polynucleotide encoding a protein controlling the transcription of the polynucleotide in (a),
    inside the cell into which the first and second expression vectors have been introduced, the transcription of the polynucleotide in (a) and the degradation of the fusion protein, which is the expression product of the polynucleotide in (a), being controlled by the presence or absence of an antibiotic inside the cell
(21) A method for controlling the expression level of the target protein inside the cell with an antibiotic, comprising
    the step of introducing the expression vector according to any of (1) to (11) above into the interior of a cell and
    regulating the concentration of antibiotic inside the cell above to regulate the expression level of the target protein
    In addition, in other aspects of the present invention, the following composition, kit, system and method for controlling the expression of the target gene are provided.
(22) A gene expression control composition for controlling, using a site-specific recombination enzyme, the expression of a target gene inside a cell by the presence or absence of an antibiotic in the cell into which an expression vector containing expressibly the target gene between and/or downstream of recombination sequences has been introduced, containing
    (a) an expression vector containing expressibly a polynucleotide encoding a fusion protein of a mutant of a repressor protein, which binds to an antibiotic, and a recombination enzyme, and
    (b) an expression vector containing expressibly a polynucleotide encoding a protein for controlling the transcription of the polynucleotide in (a).
(23) The composition according to (22) above, in which the recombination enzyme is at least one protein selected from the group consisting of:
    (a) Cre recombinase;
    (b) FLP recombinase;
    (c) phage phi 13 integrase;
    (d) phage R4 integrase;
    (e) phage TP901-1 integrase;
    (f) phage λ (lambda) integrase;
    (g) phage HK022 integrase;
    (h) β (beta) recombinase;
    (i) R recombinase;
    (j) γδ (gamma delta) resolvase;
    (k) Dre recombinase; and
    (l) phi Rv1 integrase.
(23a) The composition according to (22) above, in which the recombination enzyme is at least one protein selected from the group consisting of:
    (a) Int;
    (b) IHF;
    (c) Xis;
    (d) Fis;
    (e) Hin;
    (f) Gin;
    (g) Cin;
    (h) Tn3 resolvase;
    (i) TndX;
    (j) XerC; and
    (k) XerD.
(24) The composition according to (22) or (23) above, in which the recombination sequence contains one or more recombination sequences selected from the group consisting of:
    (a) loxP;
    (b) frt (Fkp recombination target);
    (c) attB/attP;
    (d) six;
    (e) RS;
    (f) res;
    (g) rox;
    (h) mutants, variants, and derivatives of the recombination site from (a), (b), (c), (d), (e), (f) or (g), which have retained the capability of provoking recombination.
(24a) The composition according to (22) or (23a) above, in which the recombination sequence contains one or more recombination sequences selected from the group consisting of:
    (a) psi;
    (b) dif;
    (c) cer;
    (d) frt;
    (e) att; and
    (f) mutants, variants, and derivatives of the recombination site from (a), (b), (c), (d) or (e), which have retained the capability of provoking recombination.

(25) The composition according to any of (22) to (24) above, in which the recombination enzyme is Cre recombinase and the recombination sequence is the loxP sequence.
(26) The composition according to any of (22) to (25) above, in which the target gene is a transcription factor.
(26a) The composition according to (26) above, in which the transcription factor is any of Oct3/4, Klf4, Sox2 or c-Myc gene.
(27) The composition according to any of (22) to (26) above, in which the polynucleotide in (b) encodes a protein that binds to the transcription control region of the polynucleotide in (a) and enhances the transcription of the polynucleotide, the protein being able to bind to the transcription control region only when bound to the antibiotic.
(28) The composition according to any of (22) to (27) above, in which the fusion protein, which is the expression product of the polynucleotide in (a), is degraded when not bound to the antibiotic inside the cell described above.
(29) The composition according to any of (22) to (28) above, in which the antibiotic is a tetracycline-type antibiotic.
(30) The composition according to (29) above, in which the tetracycline-type antibiotic is tetracycline or its derivative selected from doxycycline, oxytetracycline, chlortetracycline or anhydrotetracycline.
(31) The composition according to any of (22) to (30) above, in which the mutant of the repressor protein is a mutant of a tetracycline repressor protein.
(32) The composition according to (31) above, in which the mutant of the tetracycline repressor protein has an amino acid sequence comprising at least one amino acid residue substituted in the amino acid sequence of a wild-type tetracycline repressor protein.
(33) The composition according to (32) above, in which the substitution of amino acid residue is present at least any two sites among the aspartic acid at position 95, the leucine at position 101 and the glycine at position 102 of the amino acid sequence of the wild-type tetracycline repressor protein.
(34) A gene expression control kit for controlling, using a site-specific recombination enzyme, the expression of a target gene inside a cell by the presence or absence of an antibiotic in the cell into which an expression vector containing expressibly the target gene between and/or downstream of recombination sequences has been introduced, containing,
(a) an expression vector containing expressibly a polynucleotide encoding a fusion protein of a mutant of a repressor protein, which binds to an antibiotic, and a recombination enzyme, and
(b) an expression vector containing expressibly a polynucleotide encoding a protein for controlling the transcription of the polynucleotide in (a).
(35) The kit according to (34) above, in which the recombination enzyme is at least one protein selected from the group consisting of:
(a) Cre recombinase;
(b) FLP recombinase;
(c) phage phi 13 integrase;
(d) phage R4 integrase;
(e) phage TP901-1 integrase;
(f) phage λ (lambda) integrase;
(g) phage HK022 integrase;
(h) β (beta) recombinase;
(i) R recombinase;
(j) γδ (gamma delta) resolvase;
(k) Dre recombinase;
(l) phi Rv1 integrase;
(m) Int;
(n) IHF;
(o) Xis;
(p) Fis;
(q) Hin;
(r) Gin;
(s) Cin;
(t) Th3 resolvase;
(u) TndX;
(v) XerC; and
(w) XerD.
(36) The kit according to (34) or (35) above, in which the recombination sequence contains one or more recombination sequences selected from the group consisting of:
(a) loxP;
(b) frt;
(c) attB/attP;
(d) six;
(e) RS;
(f) res;
(g) rox;
(h) psi;
(i) dif;
(j) cer; and
(k) mutants, variants, and derivatives of the recombination sequence from (a), (b), (c), (d), (e), (f), (g), (h), (i) or (j), which have retained the capability of provoking recombination.
(37) The kit according to any of (34) to (36) above, in which the recombination enzyme is Cre recombinase and the recombination sequence is the loxP sequence.
(38) The kit according to any of (34) to (37) above, in which the target gene is a transcription factor.
(38a) The kit according to (38) above, in which the transcription factor is any of Oct3/4, Klf4, Sox2 or c-Myc gene.
(39) A gene expression control system for controlling, using a site-specific recombination enzyme, the expression of a target gene inside a cell by the presence or absence of an antibiotic, containing
(a) a cell
(b) an expression vector that is introduced into the interior of the above cell, and contains expressibly a polynucleotide encoding a fusion protein of a mutant of a repressor protein, which binds to an antibiotic, and a recombination enzyme,
(c) an expression vector that is introduced into the interior of the above cell, and contains expressibly a polynucleotide encoding a protein for controlling the transcription of the polynucleotide in (b),
(d) an expression vector that is introduced into the interior of the above cell, and contains expressibly a target gene between and/or downstream of recombination sequences, and
(e) an antibiotic to be introduced into the interior of the above cell,
the transcription of the polynucleotide in (b) and the degradation of the fusion protein, which is the expression product of the polynucleotide in (b), being controlled inside the cell by the presence or absence of the antibiotic, and the expression of the target gene being controlled by the expressed amount of the fusion protein.
(40) The system according to (39) above, in which the recombination enzyme is at least one protein selected from the group consisting of:
(a) Cre recombinase;
(b) FLP recombinase;
(c) phage phi 13 integrase;
(d) phage R4 integrase;
(e) phage TP901-1 integrase;
(f) phage λ (lambda) integrase;
(g) phage HK022 integrase;
(h) β (beta) recombinase;

(i) R recombinase;
(j) γδ (gamma delta) resolvase;
(k) Dre recombinase;
(l) phi Rv1 integrase;
(m) Int;
(n) IHF;
(o) Xis;
(p) Fis;
(q) Hin;
(r) Gin;
(s) Cin;
(t) Th3 resolvase;
(u) TndX;
(v) XerC; and
(w) XerD.
(41) The system according to (39) or (40) above, in which the recombination sequence contains one or more recombination sequences selected from the group consisting of:
(a) loxP;
(b) frt;
(c) attB/attP;
(d) six;
(e) RS;
(f) res;
(g) rox;
(h) psi;
(i) dif;
(j) cer;
and
(k) mutants, variants, and derivatives of the recombination sequence from (a), (b), (c), (d), (e), (f), (g), (h), (i), (or (j), which have retained the capability of provoking recombination.
(42) The system according to any of (39) to (41) above, in which the recombination enzyme is Cre recombinase and the recombination sequence is the loxP sequence.
(43) The system according to any of (39) to (42) above, in which the target gene is a transcription factor.
(43a) The system according to (43) above, in which the transcription factor is any of Oct3/4, Klf4, Sox2 or c-Myc gene.
(44) A gene expression control method for controlling, using a site-specific recombination enzyme, the expression of a target gene inside a cell by the presence or absence of an antibiotic, comprising the step of expressing, under the presence or under the absence of an antibiotic inside the cell,
(a) an expression vector containing expressibly a polynucleotide encoding a fusion protein of a mutant of a repressor protein, which binds to an antibiotic, and a recombination enzyme,
(b) an expression vector containing expressibly a polynucleotide encoding a protein for controlling the transcription of the polynucleotide in (a), and
(c) an expression vector containing expressibly a target gene between and/or downstream of recombination sequences.
(45) The method according to (44) above, in which the recombination enzyme is at least one protein selected from the group consisting of:
(a) Cre recombinase;
(b) FLP recombinase;
(c) phage phi 13 integrase;
(d) phage R4 integrase;
(e) phage TP901-1 integrase;
(f) phage λ (lambda) integrase;
(g) phage HK022 integrase;
(h) β (beta) recombinase;
(i) R recombinase;
(j) γδ (gamma delta) resolvase;
(k) Dre recombinase;
(l) phi Rv1 integrase;
(m) Int;
(n) IHF;
(o) Xis;
(p) Fis;
(q) Hin;
(r) Gin;
(s) Cin;
(t) Th3 resolvase;
(u) TndX;
(v) XerC; and
(w) XerD.
(46) The method according to (44) or (45) above, in which the recombination sequence contains one or more recombination sequences selected from the group consisting of:
(a) loxP;
(b) frt;
(c) attB/attP;
(d) six;
(e) RS;
(f) res;
(g) rox;
(h) psi;
(i) dif;
(j) cer;
and
(m) mutants, variants, and derivatives of the recombination sequence from (a), (b), (c), (d), (e), (f), (g), (h), (i) or (j), which have retained the capability of provoking recombination.
(47) The method according to any of (44) to (46) above, in which the recombination enzyme is Cre recombinase and the recombination sequence is the loxP sequence.
(48) The method according to any of (44) to (47) above, in which the target gene is a transcription factor.
(48a) The method according to (48) above, in which the transcription factor is any of Oct3/4, Klf4, Sox2 or c-Myc gene.

According to the present invention, functional analysis of a target protein, kinetic analysis of a drug by imaging, treatment of a disease with few adverse effects, and the like, can be carried out using a simple molecular system.

The tetracycline-type antibiotic (herein, sometimes abbreviated as "Tet") used in the present invention has the advantages of being extremely inexpensive compared to, for instance, rapamycin used in STANKUNAS K et al, in addition, excellent absorption and permeation within the body when used in animals, and high safety. The tetracycline-type antibiotic used in the present invention is advantageous On the points that there are an extremely large number of experimental examples of administration in mice, and that it is a drug that is already used widely in clinical setting, thus safety has been confirmed.

According to the protein degradation control method of the present invention, since no protein (for instance, a protein that is originally present inside the cell) other than the fusion protein introduced from the outside into the cell is used, superfluous influences onto the cell can be eliminated.

In addition, according to the dual control method of the present invention for gene transcription and protein degradation, a control at the transcription stage and a control of protein degradation can be realized simultaneously, simply by the addition of one species of drug. This allows the protein expression during a non-expression induced period to be suppressed almost completely, enabling a stringent control of protein expression. In addition, owing to this effect, protein expression induction efficiency is several hundreds of times when induced compared to uninduced, dramatically improved compared to induction efficiency of several tens of times in the case of transcription control only or protein degradation control only.

According to the combination of gene transcription control and protein degradation control (dual control method) of the present invention, an extremely stringent gene expression control can be realized even in a case where stringent enough expression control is difficult by gene transcription control only or protein degradation control only with an antibiotic.

BRIEF DESCRIPTION OF THE DRAWINGS

FIG. 2 (A) shows no substitution of arginine 28; and FIG. 2 (B) shows arginine at position 28 substituted with glutamine;

FIG. 4 (B) is a graph showing the changes in the intensity of fluorescence after removal of doxycycline in cells expressing mutant TetR-EGFP compared to cells simply expressing EGFP only;

FIG. 7 (A) shows untreated cells without doxycycline; FIG. 7 (B) shows cells when doxycycline was added to untreated cells; and FIG. 7 (C) shows cells with an mRNA encoding a mutant TetR-EGFP introduced and added doxycycline;

BEST MODE FOR CARRYING OUT THE INVENTION

Figure 1:
FIG. 1 (A) is a schematic of a cDNA encoding TetR-EGFP; and FIGS. (B to D) are graphs showing the results of tests of stability of wild-type TetR-EGFP and mutant TetR-EGFP using a flow cytometer.
Figure 1:
Figure 1:
Figure 1:
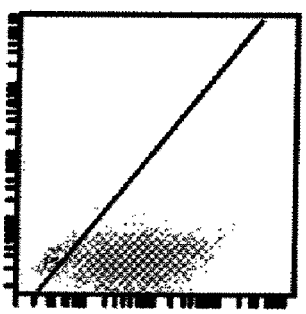
Figure 1:
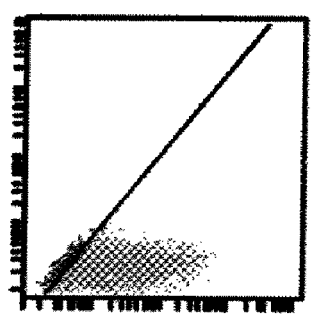
Figure 1:
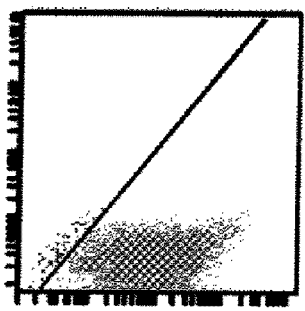
Figure 1:
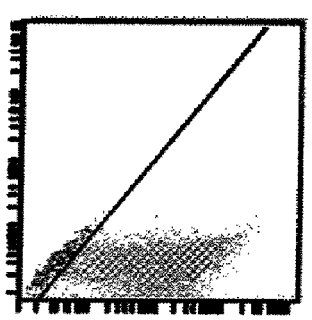

1. The Fusion Protein of the Present Invention

In one embodiment, the present invention provides a fusion protein containing a mutant protein of a protein that binds to an antibiotic and a target protein fused thereto. Here, the mutant protein is degraded when not bound to the antibiotic inside the cell and stabilized when bound to the antibiotic, the fusion protein is degraded when not bound to the antibiotic inside the cell and stabilized when bound to the antibiotic. More specifically, the present invention provides a mutant protein comprising an *Escherichia coli*-derived tetracycline repressor protein (TetR protein) into which a point mutation was introduced. In more detail, a fusion protein containing a mutant protein comprising a TetR protein into which a point mutation was introduced and a target protein fused thereto is provided.

As used herein, a "mutant protein of a protein that binds to an antibiotic" refers to a mutant of a protein having an amino acid sequence in which at least one amino acid residue is substituted, deleted, added or inserted in the amino acid sequence of a protein that binds to an antibiotic, becoming destabilized and degraded by a protease in the absence of the antibiotic while becoming stabilized and escaping degradation when bound to the antibiotic.

Examples of "antibiotics" include tetracycline-type antibiotics, penicillin-type antibiotics, chloramphenicol-type antibiotics, aminoglycoside-type antibiotics, and the like. In addition, as examples of "proteins" binding to such antibiotics, repressor proteins of the antibiotics, β-lactamase, chloramphenicol acetyltransferase, aminoglycoside 3'-phosphotransferase, and the like, may be cited. In preferred embodiments of the present invention, the antibiotic is a tetracycline-type antibiotic, and the protein binding the antibiotic is a repressor protein of the antibiotic described above.

Preferably, the repressor protein is TetR protein and the mutant protein is a mutant TetR protein. Consequently, in one embodiment, the present invention provides a fusion protein containing a mutant TetR protein and a target protein fused thereto.

Herein, "TetR protein" or "wild-type TetR protein" refers to the *Escherichia coli*-derived tetracycline repressor protein encoded by the DNA of GenBank Gene ID: 2653970 (NCBI protein database accession number: NP_941292 (SEQ ID: 2); CDS: NC_005211 (SEQ ID: 1)).

Herein, "mutant TetR protein" refers to a mutant of TetR protein having an amino acid sequence in which at least one amino acid residue is substituted, deleted, added or inserted in the amino acid sequence of the TetR protein above, becoming destabilized and degraded by a protease in the absence of tetracycline-type antibiotic while becoming stabilized and escaping degradation when bound to a tetracycline-type antibiotic.

Preferably, the mutant TetR protein has an amino acid sequence comprising at least two amino acid residues substituted in the amino acid sequence of the wild-type TetR protein. More preferably, the amino acid residue substitution described above exists at least any two sites among the aspartic acid at position 95, the leucine at position 101 and the glycine at position 102 in amino acid sequence of the wild-type TetR protein. Most preferably, the mutant TetR protein has an amino acid sequence having, among the mutations substituting the aspartic acid at position 95 with an asparagine, the leucine at position 101 with a serine, and the glycine at position 102 with an aspartic acid in the amino acid sequence of the wild-type TetR protein, any two at least or all three of the mutations described above. The embodiment of mutation in the amino acid sequence of the mutant TetR protein is not limited to the substitution of an amino acid residue, but may be a deletion, addition and/or insertion of one or more amino acid residues in the wild-type TetR protein. In addition, the positions of amino acids having such mutations are not limited to those exemplified above.

In the context of the fusion protein of the present invention, a "target protein" is deemed to mean a protein, such as (1) fluorescent protein or luminescent protein (2) therapeutic protein (3) protein to be subjected to functional analysis, (4) recombination enzyme, or the like that allows an industrially useful effect to be obtained by controlling the degradation (or stability or activity) of the protein using a mutant TetR protein and Tet. In such cases where the target protein is a well-known protein, in general, the nucleotide sequence of the gene coding this can be obtained from a variety of publicly usable sequence databases (for instance, GenBank database). In addition, when the amino acid sequence of the target protein or the nucleotide sequence coding therefor is unidentified, the amino acid sequence of the protein and the nucleotide sequence coding therefor can be determined using sequencing methods well known to those skilled in the art (for instance, refer to Sambrook & Russell, Molecular Cloning; A Laboratory Manual, Third Edition, 2001, Cold Spring Harbor Laboratory Press, Cold Spring Harbor, N.Y., and the like).

The fusion protein of the present invention may be created according to ordinary methods in the field. Briefly, it is possible to ligate a cDNA encoding the target protein with a cDNA encoding a mutant TetR protein to construct a DNA encoding a fusion protein of the target protein and the mutant TetR protein, insert this DNA, for instance, into an expression vector for use in eukaryotes, and introduce this expression vector into a eukaryote to be expressed (for instance, refer to the above Sambrook & Russell).

As examples of "fluorescent protein" used in the embodiments of the present invention, Green Fluorescent Protein (GFP), Enhanced Green Fluorescent Protein (EGFP), Cyan Fluorescent Protein (CFP), Enhanced Cyan Fluorescent Protein (ECFP), Yellow Fluorescent Protein (YFP), Enhanced Yellow Fluorescent Protein (EYFP), Red Fluorescent Protein DsRed and mutants thereof (DsRed2, DsRed-express, Timer, mRFP1 and mutants thereof, and the like), AmCyan, ZsGreen, ZsYellow, AsRed, HcRed, Kusabira Orange, Kaede, Azami Green, and the like, may be cited.

As examples of "luminescent protein" used in embodiments of the present invention, firefly luciferase, renilla luciferase, jelly fish aequorin, and the like, may be cited. These fluorescent proteins or luminescent proteins are commercialized by providers well known to those skilled in the art (for instance, Clontech, Promega and the like).

Herein, "therapeutic protein" means a protein that is effective in the prevention and/or treatment of a disease and includes, for instance, cytokines, which activate cells playing a part in immunity (for instance, human interleukin2, human granulocyte-macrophage colony stimulating factor, human macrophage colony stimulating factor, human interleukin12, etc.), and the like. In addition, in order to kill cancer cells and the like directly, toxins such as ricin and diphtheria toxin, or herpes virus thymidine kinase in combination with the antiviral agent ganciclovir can also be used. In addition, antibodies and the like can also be used. For instance, regarding fusion protein with an antibody, it is possible to ligate a cDNA encoding an antibody or an antibody fragment with a cDNA encoding a mutant TetR protein to construct a DNA encoding a fusion protein of the antibody and the mutant TetR protein, insert this DNA, for instance, into an expression vector for use in eukaryotes, and introduce this expression vector into a eukaryote to be expressed. Or, in order to carry out delivery of a therapeutic protein that is site-specific to a specific antigen inside a biological tissue, it is also possible to construct a DNA encoding a fusion protein of an antibody against the antigen, a therapeutic protein and a mutant TetR protein, insert this DNA, for instance, into an expression vector of a eukaryote, and introduce this expression vector into a eukaryote to be expressed. Or, such a fusion protein may be created ex vivo and then introduced into an organism.

In addition, as examples of "protein to be subjected to functional analysis" used in other embodiments of the present invention, protein kinases, transcription factors, and the like, may be cited. As examples of protein kinases, for instance, MAPK family kinases, PKC family kinases, PKA family kinases, Src family kinases, Jak family kinases, Abl family kinases, IKK family kinases, and the like, may be cited. As examples of transcription factors, RUNX family, STAT family, nuclear receptor, leucine zipper family, NF-κB family and the like, exist.

The fusion protein of the present invention described above is unstable in the absence of a tetracycline-type antibiotic but stabilizes when bound to a tetracycline-type antibiotic. Consequently, since the fusion protein of the present invention enables a control of the degradation of a target protein by the concentration of a tetracycline-type antibiotic, the fusion protein of the present invention can be used for in vivo imaging using a fluorescent or luminescent protein, controlling of the action of a therapeutic protein, functional analysis of a protein in vivo, and the like.

As "tetracycline-type antibiotic (Tet)" used in the present invention, there is no particular limitation as long as it binds to the mutant TetR protein of the present invention stabilizing the structure thereof and inhibiting degradation by proteolytic enzymes, and for instance, tetracycline, and, doxycycline, oxytetracycline, chlortetracycline and anhydrotetracycline, which are derivatives of tetracycline may be cited.

2. Regulation of the Expression of a Target Gene by the Dual Control System of the Present Invention Including a Regulation of Gene Expression and a Regulation of Protein Degradation In other aspects of the present invention, in order to control the expression of a target gene inside a cell by the presence or absence of an antibiotic, a system, a composition, a kit and a method for controlling the expression of a target gene using a site-specific recombination enzyme are provided.

In one embodiment, the present invention provides an expression control composition for controlling, using a site-specific recombination enzyme, the expression of a target gene inside a cell by the presence or absence of an antibiotic in the cell into which an expression vector containing expressibly the target gene between and/or downstream of recombination sequences has been introduced. This composition contains:
(a) an expression vector containing expressibly a polynucleotide encoding a fusion protein of a mutant of a repressor protein, which binds to an antibiotic, and a recombination enzyme, and
(b) an expression vector containing expressibly a polynucleotide encoding a protein for controlling the transcription of the polynucleotide in (a). Here, the intracellular transcription of the polynucleotide in (a) and degradation of the fusion protein, which is the expression product of the polynucleotide in (a), are controlled by the presence or absence of an antibiotic. In addition, the expression of the target gene is controlled by the amount of expression of the fusion protein.

In another embodiment of the present invention, provided is an expression control kit for controlling, using a site-specific recombination enzyme, the expression of a target gene inside a cell by the presence or absence of an antibiotic in the cell into which an expression vector containing expressibly the target gene between and/or downstream of recombination sequences has been introduced. This kit contains:
(a) an expression vector containing expressibly a polynucleotide encoding a fusion protein of a mutant of a repressor protein, which binds to an antibiotic, and a recombination enzyme, and
(b) an expression vector containing expressibly a polynucleotide encoding a protein for controlling the transcription of the polynucleotide in (a). Here, the intracellular transcription of the polynucleotide in (a) and degradation of the fusion protein, which is the expression product of the polynucleotide in (a), are controlled by the presence or absence of an antibiotic. In addition, the expression of the target gene is controlled by the amount of expression of the fusion protein.

In a further embodiment of the present invention, an expression control system for controlling, using a site-specific recombination enzyme, the expression of a target gene inside a cell by the presence or absence of an antibiotic is provided. This system contains:
(a) a cell
(b) an expression vector that is introduced into the interior of the above cell, and contains expressibly a polynucleotide encoding a fusion protein of a mutant of a repressor protein, which binds to an antibiotic, and a recombination enzyme,
(c) an expression vector that is introduced into the interior of the above cell, and contains expressibly a polynucleotide encoding a protein for controlling the transcription of the polynucleotide in (b),
(d) an expression vector that is introduced into the interior of the above cell, and contains expressibly a target gene between and/or downstream of recombination sequences, and
(e) an antibiotic to be introduced into the interior of the above cell, the transcription of the polynucleotide in (b) and the degradation of the fusion protein, which is the expression product of the polynucleotide in (b), being controlled inside the cell by the presence or absence of the antibiotic, and the expression of the target gene being controlled by the expressed amount of the fusion protein.

In an even further embodiment of the present invention, a method for controlling, using a site-specific recombination enzyme, the expression of a target gene inside a cell by the presence or absence of an antibiotic is provided. This method contains the step of expressing under the presence or under the absence of an antibiotic inside the cell,
(a) an expression vector containing expressibly a polynucleotide encoding a fusion protein of a mutant of a repressor protein, which binds to an antibiotic, and a recombination enzyme,
(b) an expression vector containing expressibly a polynucleotide encoding a protein for controlling the transcription of the polynucleotide in (a), and
(c) an expression vector containing expressibly a target gene between and/or downstream of recombination sequences.
Here, the intracellular transcription of the polynucleotide in (a) and degradation of the fusion protein, which is the expression product of the polynucleotide in (a), are controlled by the presence or absence of an antibiotic. In addition, the expression of the target gene is controlled by the amount of expression of the fusion protein.

"Recombination enzyme" used in the present invention refers to a recombination enzyme that mediates site-specific recombination between a plurality of specific DNA sequences (recombination sequences). Examples of "recombination enzyme" and "recombination sequence" used in the present invention include recombination enzymes/recombination sequences described in Garcia-Otin & Guillou, "Mammalian genome targeting using site-specific recombinases", Frontiers in Bioscience 11, 1108-1136, Jan. 1, 2006, and WO2001/042509 (Japanese National-phase PCT Laid-Open Patent Publication No. 2004-500061) (these references are all concretely incorporated herein as references). Among them, Cre recombinase/loxP sequence may be cited as a representative example of recombination enzyme/recombination sequence.

loxP (locus of crosscover (x) in P1) is a sequence spanning 34 base pairs (bp), comprising an 8 bp asymmetric central sequence (this defines the orientation of the loxP element) and two 13 bp palindromic sequences adjacent to this. Cre recombinase (herein, sometimes abbreviated simply as "Cre") has an important function as a resolvase in the replication cycle of the P1 bacteriophage, cutting and rejoining the duplicated genomes of the phage into two analogous particles. Cre recombinase is a 343 amino acid (aa)/38 kDa protein that functions as a tetrameric complex that does not require a cofactor. Cre is capable of recombining two loxP sites (sequences) in either of when these are located on the same DNA strand and when located on different DNA strands. When two loxP sequences are present on the same DNA strand, if these are oriented in the same direction, a reaction excising the DNA segment present between the two loxP sequences occurs. The excised portion becomes a circular particle, and the loxP sequences remain on each DNA portion (for instance, refer to FIG. 10).

The control of the expression of a target gene can be carried out using such site-specific recombination enzyme and recombination sequence in combination with the method of the present invention of controlling the expression of a target protein inside a cell with an antibiotic. That is to say, the expression of a target gene can be controlled by the presence/absence (or the concentration) of an antibiotic, by introducing into the interior of a cell and expressing (c) an expression vector carrying expressibly a DNA segment of a target gene between and/or downstream of two recombination sequences (example: loxP), (a) an expression vector containing expressibly a polynucleotide encoding a fusion protein of a mutant of a repressor protein, which binds to an antibiotic, and a recombination enzyme (example: Cre recombinase), and (b) an expression vector containing expressibly a polynucleotide encoding a protein for controlling the transcription of the polynucleotide encoding the fusion protein (example: artificial transcription factor rtTA). Here, the target gene on the vector is not limited to one, and a plurality may be present. For instance, it should be understandable for those skilled in the art that linking and using a first target gene between two recombination sequences and a second target gene downstream of two recombination genes is also possible.

According to such a gene expression control system of the present invention, for instance, using the Cre/loxP system, the expression of Cre recombinase can be controlled by the presence or absence (or the concentration) of an antibiotic (example: doxycycline), and furthermore, the expression of the target gene can be controlled by the presence or absence of Cre recombinase. More specifically, since the expression of Cre recombinase is inhibited at the transcription level and the protein level in the absence of the antibiotic, the excision of the gene segment between the loxP sites by the action of the Cre recombinase does not occur, the expression of the target gene is maintained. Meanwhile, since the expression of the fusion protein of Cre recombinase and mutant TetR is inhibited neither at the transcription level nor at the protein level in the presence of the antibiotic, the target gene segment sandwiched between the loxP sites is excised by the action of Cre from the fusion protein (Cre recombinase+mutant TetR), which is the expression product, inhibiting the expression of this target gene. In addition, here, for instance, if a second target gene were linked downstream of two loxP sequences, the expression of the second target gene can be made to occur after the target gene between the loxP sites is excised.

For instance, Oct3/4, Klf4, Sox2 and/or c-Myc genes can be used as target genes. The Oct3/4, Klf4, Sox2 and c-Myc genes are considered to be necessary for the transformation of skin cells into iPS cells (induced pluripotent stem cells); however, a known problem is that they induce malignant transformation of cells after iPS transformation. According to the target gene expression control method of the present invention, a gene expression control becomes possible, in which the genes described above are let to express in the absence of antibiotic while they are required for iPS transformation of cells, and when the iPS cells are differentiated and they are no longer necessary, the expression of the above genes that are the causes of malignant transformation of cells is inhibited in the presence of an antibiotic. Here, "target genes" used in the present invention include any genes requiring a control of the expression thereof, and it should be understandable to those skilled in the art that, in addition to Oct3/4, Klf4, Sox2 and c-Myc genes, for instance, various transcription factor groups known to be involved in cell differentiation and tissue-specific functions, for instance, Hox gene cluster and non-Hox gene cluster from the homeobox gene cluster, fork head gene cluster, T box gene cluster, polycomb gene cluster, Trithorax gene cluster, GATA gene cluster, Maf gene cluster and Hes gene cluster, transcription factors involved in cell stress response, ATF-2, Nrf2, HSF1, HIF and the like, or, of the kinases involved in intracellular signal transduction, MAP kinase, protein kinase A, protein kinase C, protein kinase D, protein kinase G, and the like, from the serine-threonine kinase group, Src kinase group, receptor kinase group, and the like, from the tyrosine kinase group, can also be used.

As examples of recombination enzyme/recombination sequence (site) system other than Cre recombinase/loxP system that may be used together with the system for transcription and expression dual control of protein of the present invention, for instance, Flp recombinase/frt (Fkp recombination target) site, phage phi13 integrase/att site, phage R4 integrase/att site, phage TP901-1 integrase/att site, phage lambda integrase/att site, phage HK022/att site, beta recombinase/six site, gamma delta resolvase/res site, Dre recombinase/rox site, phi Rv1 integrase/att site, and the like, may be cited (Garcia-Otin & Guillou (cited above)).

As further examples of recombination enzymes, lambda Int protein, IHF, Xis, F is, Hin, Gin, Cin, Th3 resolvase, TndX, XerC and XerD are included. As recombination sequences (sites), loxP site, frt site, att site, six site, res site, rox site, psi site, dif site and cer site are included (WO2001/042509 (Japanese National-phase PCT Laid-Open Patent Publication No. 2004-500061)).

In preferred embodiments of the system, the composition, the kit or the method for controlling the expression of a target gene using a site-specific recombination enzyme by the dual control system of the present invention including gene expression regulation and protein degradation regulation, a nuclear export sequence (NES) may be added on the C-terminal side of the DNA segment encoding a recombination enzyme in order to raise the recombination efficiency (refer to Example 8).

3. Polynucleotide and Expression Vector of the Present Invention, and Host Transfected Using this In another embodiment, the present invention provides a polynucleotide encoding a fusion protein of the present invention. In addition, the present invention provides an expression vector containing the polynucleotide encoding a fusion protein of the present invention. Preferably, the expression vector of the present invention contains an expression cassette containing the following constitutive elements (a) to (c):

(a) a promoter transcribable inside a host cell
(b) a polynucleotide encoding a fusion protein of the present invention linked to the promoter; and
(c) a signal functioning inside the host cell in relation to transcription termination and polyadenylation of an RNA molecule.

As a promoter and transcription termination signal (terminator), a combination suitable for increasing the efficiency of gene expression is used according to the host into which the expression cassette described above is introduced. Those skilled in the art can select such a suitable combination. As non-limiting examples of such expression vectors, the expression vector pEB6CAG used in EXAMPLES of the present patent application, which is replicated and maintained stably in human cells, may be cited; this contains CAG promoter as a promoter, a mutant TetR-EGFP as a fusion protein and SV40 polyA sequence as a transcription termination signal sequence.

In addition to the expression cassette described above, the expression vector of the present invention may contain another constitutive element. Non-limiting examples of such other constitutive elements include an IRES sequence and a cDNA downstream thereof that allows expression of a fluorescent protein such as a tandem dimer of DsRed, which are inserted between the mutant TetR-EGFP and SV40 polyA, as used in EXAMPLES of the present specification.

In addition, expression units or expression vectors that may be used for expressing the fusion protein of the present invention inside a cell or an organism include expression units and the like, which are found for instance in plasmid pcDNA3 (Invitrogen), plasmid AH5, pRC/CMV (Invitrogen), pCAGGS, pCXN2, pME18S, pEF-BOS, and the like, can be used. Introduction of a gene into an expression unit and/or vector may be achieved using such gene manipulation techniques as described in manuals such as, for instance, Molecular Cloning & Current Protocols in Molecular Biology, Sambrook, J. et al., Molecular Cloning, Cold Spring Harbor Press (1989); Ausbel. F. M. et al., Current Protocols in Molecular Biology, Green Publishing Associates and Wiley-Interscience (1989). The generated expressible polynucleotide may be introduced in an expressible form (for instance, as naked plasmid or other DNA in a targeting liposome or as part of a viral vector) into the cell of a subject (for instance, human subject) by any methods that may place a polynucleotide into a cell. Gene introduction methods include direct injection into tissue or affected area (for instance, tumor), transfection by liposome (Fraley et al., Nature 370: 111-117 (1980)), receptor-mediated endocytosis (Zatloukal et al., Ann. N.Y. Acad. Sci. 660:136-153 (1992)), and particle bombardment-mediated gene transfer (Eisenbraun et al., DNA & Cell. Biol. 12:791-797 (1993)), and the like.

Figure 12:
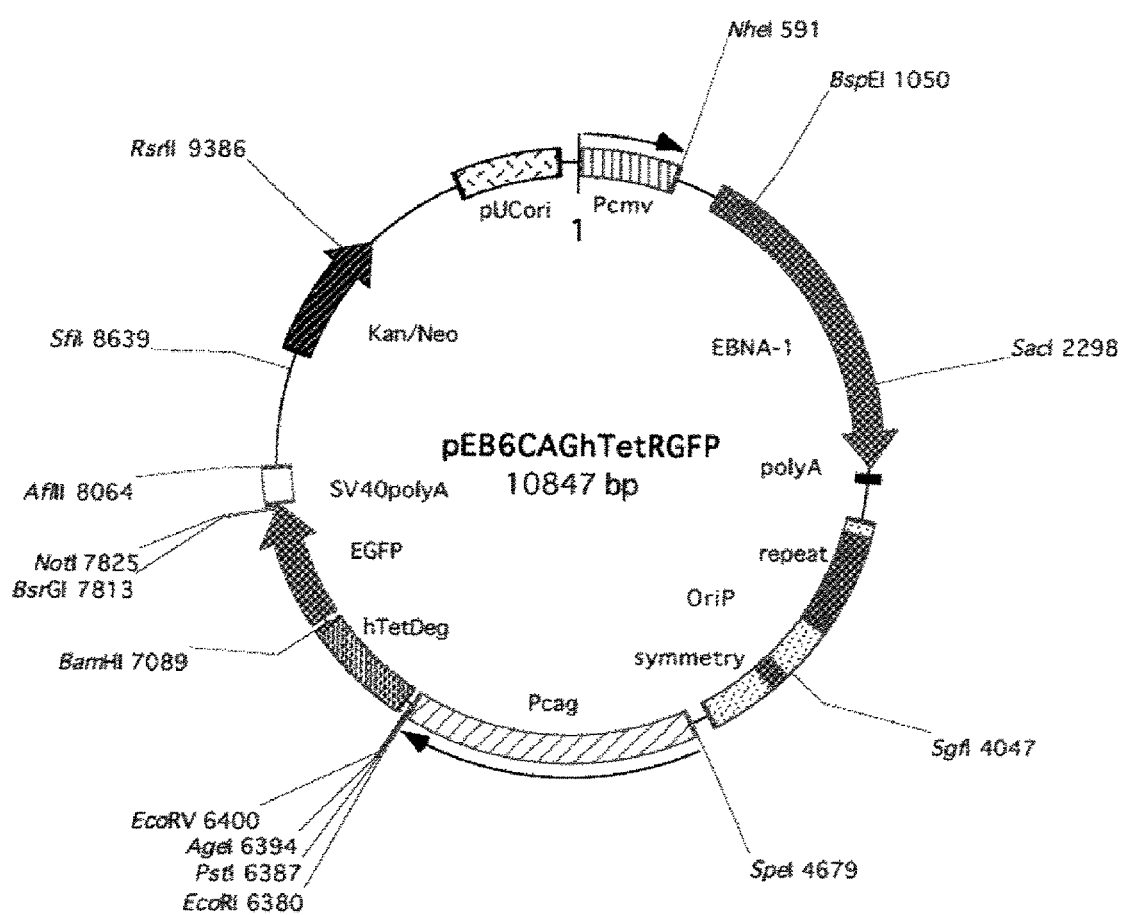
FIG. 12 is a schematic showing an example of representative expression vector used when carrying out a control on the amount of protein (control of protein degradation) inside a cell with an antibiotic, the case where EGFP was used as the target protein being shown.
Figure 13:
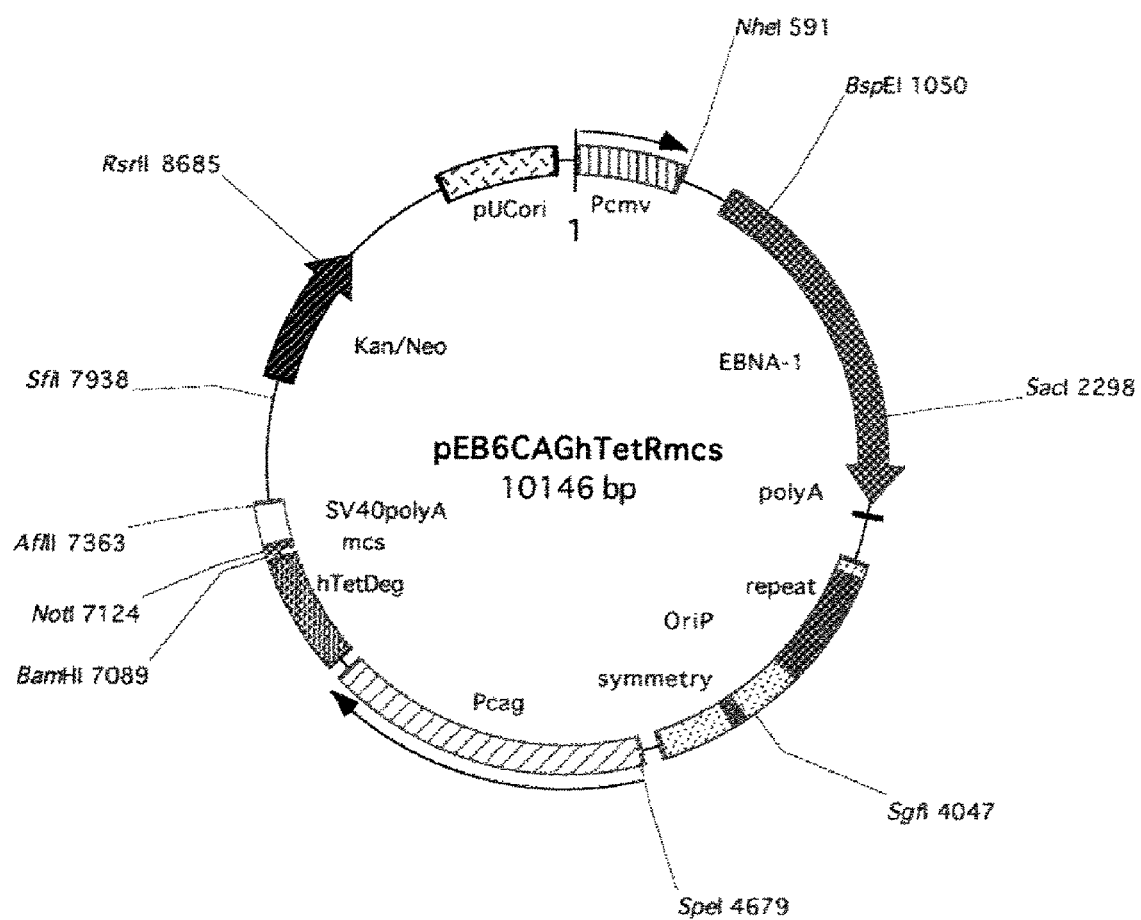
FIG. 13 is a schematic showing another example of representative expression vector used when carrying out a control on the amount of protein (control of protein degradation) inside a cell with an antibiotic; mcs being inserted so that, as the target protein, an arbitrary one can be used.

Examples of representative expression vectors used for the control of the degradation of the target protein inside a cell according to one embodiment of the present invention are shown in FIG. 12 and FIG. 13. FIG. 12 shows an example using EGFP as the target protein. FIG. 13 shows an example that is used when the insertion of a gene of another arbitrary protein as the target protein (for instance, therapeutic protein, protein to be subjected to functional analysis) is desired, with a multicloning site (mcs) inserted instead of the EGFP gene.

In a yet another embodiment, the present invention provides an expression vector in which a polynucleotide enabling a control of the transcription of the polynucleotide encoding a fusion protein of the present invention has been further integrated in the expression vector described above. According to such an expression vector, in addition to the control of protein degradation by an antibiotic, a control of the transcription of the gene becomes possible simultaneously (dual control of protein expression inside the cell).

Figure 14:
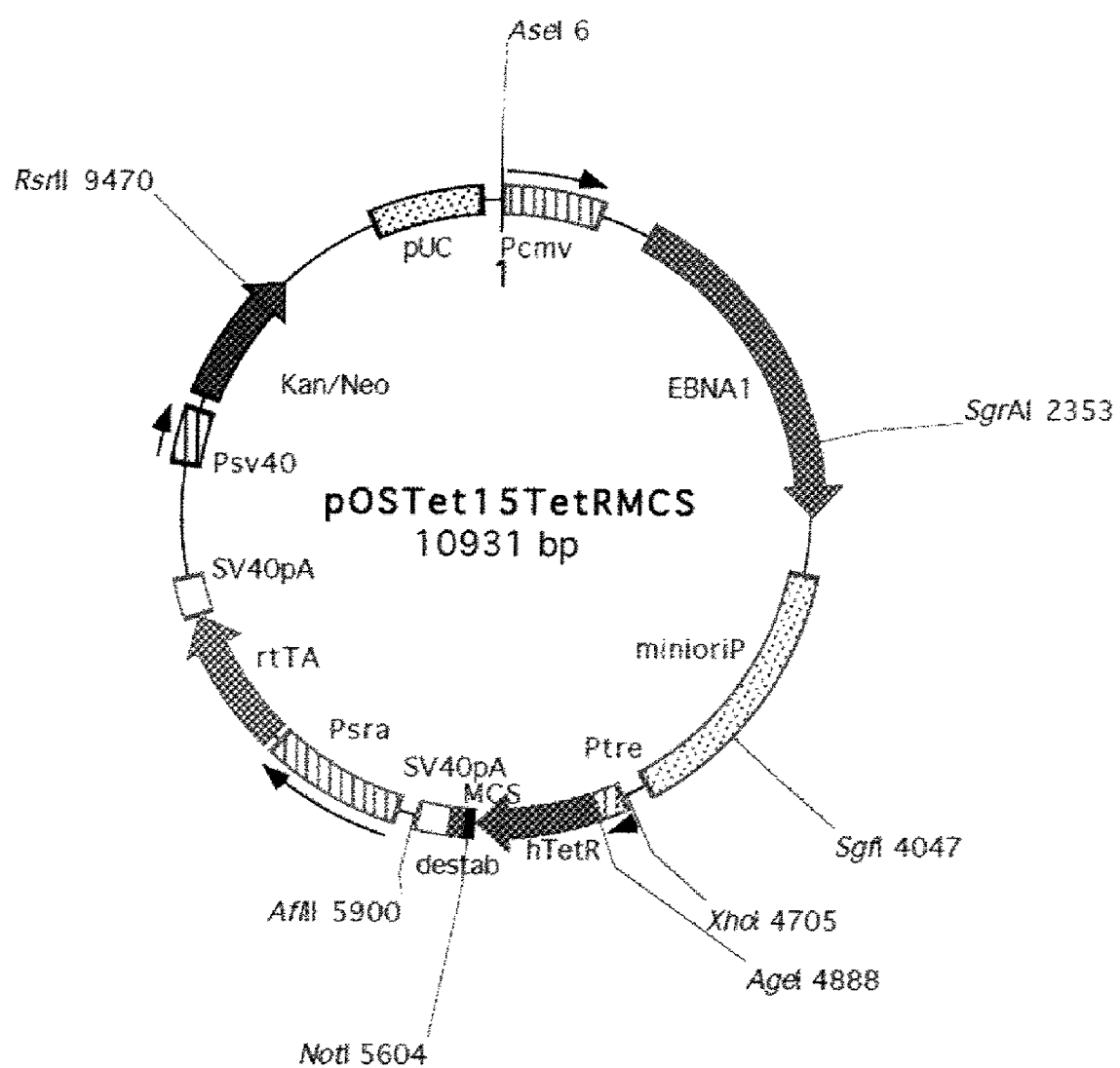
FIG. 14 is a schematic showing a representative expression vector used when carrying out control on both the gene transcription level and protein degradation level (dual control) with an antibiotic; the target protein insertion site being mcs.

An example of representative expression vector used when a control both at the gene transcription level and at the protein degradation level (dual control) by an antibiotic is carry out according to one embodiment of the present invention, is shown in FIG. 14. The structure of this vector is constituted mainly by four units.

(1) EBV Replicon Unit
  Contains the CMV promoter, EBNA-1 cDNA and oriP (region bound to by the EBNA-1 protein to carry out the replication of the vector in human cells).
(2) Objective Protein Expression Unit
  Contains the TRE promoter (own modifications), hTetR, MCS, an RNA destabilization sequence and SV40 polyA.

(3) Artificial Transcription Factor Expression Unit for Transcription Control
  Contains the SRα promoter, the artificial transcription factor rtTA and SV40 polyA.
(4) Shuttle Vector Function Unit
  Contains the amp promoter (not shown in Fig.), the SV40 promoter, the drug-resistance genes Kan/Neo, thymidine kinase polyA (not shown in Fig.), and pUC ori (replication in *Escherichia coli*).

By using a vector with such a constitution allows, only one vector needs to be introduced into a cell to enable a control of the transcription of the gene of a target protein and a control of the degradation of the protein.

Note that those skilled in the art understand that, instead of the both units of (2) and (3) described above being carried by only one vector and expressed, the unit of (2) and the unit of (3) may each be carried by a different expression vector from each other and used inside the cell.

Regarding the TetR gene contained in the unit of (2), note that the *E. coli*-derived eTetR gene can also be used instead of the human-derived hTetR gene. hTetR and eTetR can be used in separate ways according to the purposes.

hTetR is used when an as high as possible expression is desired to be secured during expression induction.

eTetR is used when an extremely stringent inhibition (low expression) is desired during non-expression induction.

This is because synthesis of a protein tends to become slow in general and the expression level become low when the base sequence is translated into amino acids if an *Escherichia coli*-derived one (eTetR) is used in a human cell, since codons with low frequencies in human cells are used. If TetR derived from human (hTetR) is used in human cells, the translation efficiency increases, allowing the expression level to be raised. In this way, separate uses according to the purposes facilitate realization of a more desirable expression regulation system.

Figure 15:
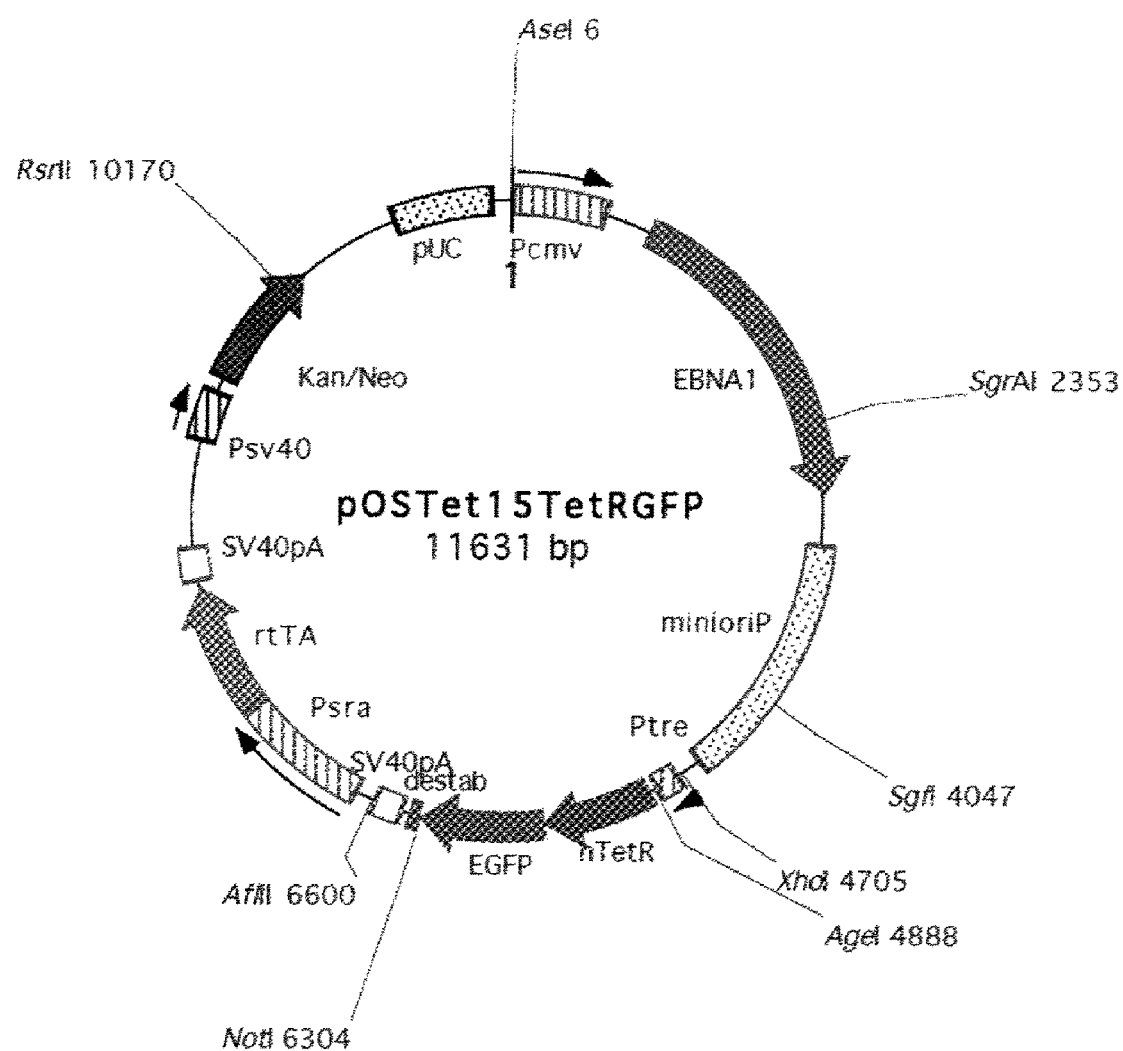
FIG. 15 is a schematic showing a representative expression vector used when carrying out control at both the gene transcription level and protein degradation level (dual control) with an antibiotic, the mode in which EGFP was used as the target protein being shown.

FIG. 15 shows an example of expression vector when the target protein is EGFP in an expression vector having a structure that is substantially similar to that shown in FIG. 14.

In one representative embodiment of the dual control method of intracellular protein expression by an antibiotic according to the present invention, a cDNA encoding a fusion protein of a mutant TetR and a target protein, which degradation regulation is possible by doxycycline, is integrated into a vector "pOSTet15", which regulated expression is possible at the transcription level, to construct a vector designated "pOSTet15-eTetR-cDNA" or "pOSTet15-hTetR-cDNA" (refer to FIG. 14 or FIG. 15).

Figure 16:
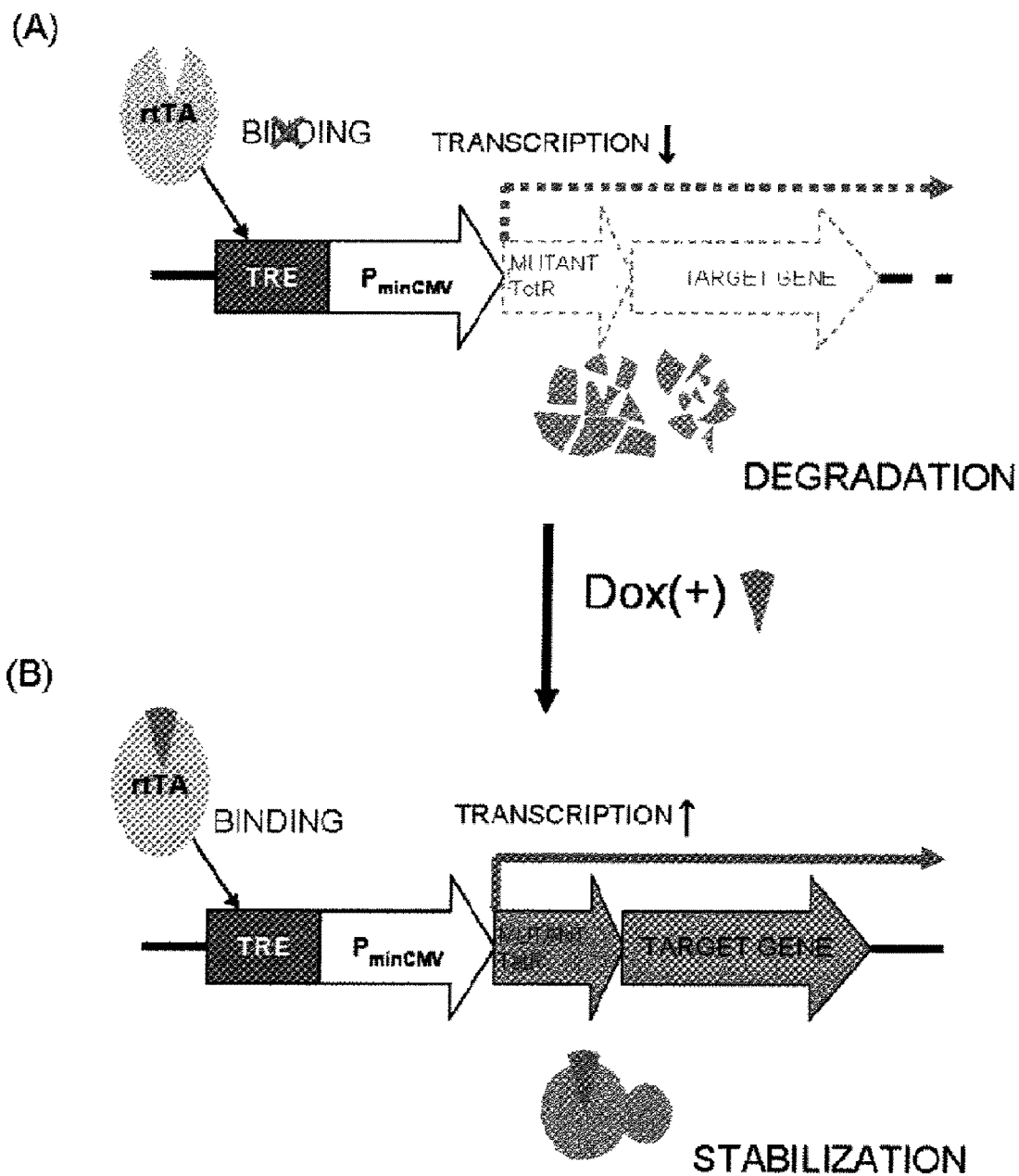
FIG. 16 shows schematics describing the principles of the system for antibiotic-mediated transcription/degradation control (dual control) of protein of the present invention.

FIG. 16 is a schematic describing the principles of the system for the transcription/degradation control (dual control) of protein by an antibiotic of the present invention. This figure shows an example in which doxycycline is used as the antibiotic (element indicated with a wedge-shape in the figure). In the absence of doxycycline (FIG. 16 (A)), since the artificial transcription factor rtTA not bound to doxycycline cannot bind to the transcription control region (corresponding to TRE in FIG. 16), the amount of transcription is low, and even the proteins produced by the slight occurrence of transcription undergo degradation by the proteolytic control mechanism of the present invention; as a result, the protein expression is inhibited stringently. In the presence of doxycycline (FIG. 16 (B)), since rtTA binds to the transcription control region, the amount of transcription increases, furthermore, the produced proteins are also stabilized by the binding of doxycycline, the amount of protein expressed becomes extremely high. In this way, the on/off states of protein expression inside the cell may be controlled explicitly.

According to the present invention, by integrating a polynucleotide for transcription control and a polynucleotide for protein degradation control in one vector, introducing one species of vector into a cell is sufficient to enable a dual control of the expression of the cDNA introduced.

In one embodiment, the present invention further provides a host cell or a host organism into which the polynucleotide described above has been introduced, or which has been transfected with the expression vector described above. Non-limiting examples of such host organisms and host cells include vertebrates and cells thereof, and fish, amphibians, reptiles, avians, mammals and the like, for instance, or cells thereof may be used. In addition, insects and cells thereof may be used. Examples of mammals include humans, mice, rats, rabbits, sheep, pigs, cows, horses, birds, cats, dogs, monkeys, chimpanzees, and the like. More concrete examples of host cells or host organisms include but not limited to human cells, mice, fertilized eggs of zebrafish, and the like, used in the examples of the present patent application.

4. Composition Containing the Fusion Protein of the Present Invention or a Polynucleotide Encoding the Fusion Protein In still another embodiment, the present invention provides a composition containing the fusion protein of the present invention, a composition containing a polynucleotide encoding the fusion protein of the present invention, a composition containing an expression vector containing the polynucleotide encoding the fusion protein the present invention, as well as a composition containing an expression vector containing the polynucleotide encoding the fusion protein the present invention and a polynucleotide for controlling the expression of the polynucleotide. These compositions of the present invention are used in combination with an antibiotic that binds to the fusion protein described above. For instance, when the fusion protein contains a mutant form of repressor protein of the tetracycline-type antibiotic, the composition of the present invention is used in combination with a tetracycline-type antibiotic (tetracycline and doxycycline, oxytetracycline, chlortetracycline or anhydrotetracycline, which are derivatives of tetracycline).

In one preferred embodiment, the composition of the present invention contains a fusion protein of a fluorescent protein or a luminescent protein and a mutant protein of a protein that binds to an antibiotic, or contains an expression vector containing a polynucleotide encoding such a fusion protein. Examples of preferred mutant proteins are mutant TetR proteins, and examples of preferred fluorescent proteins or luminescent proteins are the same as those mentioned already in the description of the fusion protein of the present invention. Preferred mutant TetR proteins are the same as those mentioned already in the description of the fusion protein of the present invention. Preferably, in order to prevent a bias of the fluorescence towards the interior of the cell nucleus, the mutant TetR protein may further have an amino acid residue substitution of arginine with glutamine at position 28. Since the degradation of the fusion protein of the present invention may be controlled by the concentration of Tet, the composition of the present invention can be used for detecting and imaging the amount of a tetracycline-type antibiotic inside a cell or inside an organism, and can be used for monitoring the kinetics of a drug.

In another embodiment, the composition of the present invention contains a fusion protein of a therapeutic protein and a mutant protein of a protein that binds to an antibiotic, or contains an expression vector containing a polynucleotide encoding such a fusion protein. Examples of preferred mutant proteins are mutant TetR proteins, and examples of proteins for therapeutic use are the same as those mentioned already in the description of the fusion protein of the present invention. Preferred mutant TetR proteins are the same as those mentioned already in the description of the fusion protein of the present invention. As a gene therapy, when an exogenous gene is introduced into a patient to improve the symptoms by the action of the protein, which is the gene product thereof, there is the danger that this protein becomes an antigen and triggers an unexpected adverse effect. Thus, for instance, if a gene encoding a therapeutic protein and a fusion gene of mutant TetR, are introduced using the composition of the present invention, the amount of fusion protein expressed, which is the expression product thereof, can be controlled with Tet, such that a treatment becomes possible while suppressing the adverse effects by administering Tet according to the situation of the patient.

In a further other embodiment, the composition of the present invention contains a fusion protein of a protein to be subjected to functional analysis and a mutant protein of a protein that binds to an antibiotic, or contains an expression vector containing a polynucleotide encoding such a fusion protein. Examples of preferred mutant proteins are mutant TetR proteins, and examples of proteins to be subjected to functional analysis are the same as those mentioned already in the description of the fusion protein of the present invention. Preferred mutant TetR proteins are the same as those mentioned already in the description of the fusion protein of the present invention. If, for instance, a fusion protein of a mutant TetR and a target protein, which is the subject of a functional analysis, is expressed by a cell using the composition of the present invention, the amount of the target protein inside the cell can be controlled by the amount of Tet added. This allows the effects exerted by the target protein on cells and individual organisms to be analyzed experimentally.

When the composition of the present invention is used for the purposes of diagnostics and/or treatments such as treatment of a disease and imaging or monitoring of pharmacokinetics in vivo, or functional analysis of protein in vivo and the like, the composition of the present invention may further contain a pharmacologically acceptable carrier, diluent or excipient, and may be provided as a medicinal composition suitable for peroral or parenteral administration.

For instance, compositions for oral administration may be in solid or liquid formulation including, concretely, tablets (including sugar-coated tablets and film-coated tablets), pills, granules, powders, capsules (including soft capsules), syrups, emulsions, suspension and the like. Such a composition is prepared by well-known methods and contains a carrier, a diluent or an excipient conventionally used the field of formulation. For instance, lactose, starch, cane sugar, magnesium stearate, and the like, may be used as carriers and excipients for tablets. In addition, as formulations of the composition for parenteral administration, for instance, injections, suppositories, and the like, are included; the injections including formulations such as intravenous injections, subcutaneous injections, intracutaneous injections, intramuscular injections, drip infusion injections and the like. Such injections are prepared according to well-known methods, for instance, by dissolving, suspending or emulsifying the fusion protein of the present invention or an expression vector containing a polynucleotide coding therefor in a sterile aqueous or oil-based solution used conventionally for injections. As aqueous solutions for injection, for instance, physiological saline, isotonic solution containing glucose or other adjuvant, and the like are used, which may be used in combination with a suitable dissolution adjuvant, for instance, an alcohol (example: ethanol), a polyalcohol (examples: propylene glycol and polyethyleneglycol), a non-ionic surfactant (example: polysorbate 80, HCO-50 (polyoxyethylene (50 mol) adduct of hydrogenated castor oil)), or the like. As oil-based solutions, for instance, sesame oil, soybean oil and the like are used, and as dissolution adjuvants benzyl benzoate, benzyl alcohol, and the like, may be used in combination. The prepared injection is conventionally filled into a suitable ampoule. Suppositories used for rectal administration are prepared, for instance, by mixing the fusion protein or an expression vector containing the polynucleotide encoding the fusion protein with a conventional base for suppositories.

It is desirable that the medicinal composition for peroral use or parenteral use described above is prepared into a formulation with a unit dose that conforms to the dosage of the active constituent. Formulations with such unit dose include, for instance, tablets, pills, capsules, injections (ampoules), suppositories, and the like, and it is desirable that they contain the active constituent described above at 5 to 500 mg per respective unit dose formulation in general, 5 to 100 mg for injections, and 10 to 250 mg for other formulations. Since a formulation obtained in this way is safe and of low toxicity it can be administered perorally or parenterally, for instance, to a human or a warm-blooded animal (for instance, mouse, rat, rabbit, sheep, pig, cow, horse, bird, cat, dog, monkey, chimpanzee, and the like).

The dose of antibiotic (for instance, tetracycline-type antibiotic) to administer in order to prevent the degradation of the fusion protein of the present invention varies with the target disease, the subject of administration, administration route, and the like. For instance, when administering orally, generally in an adult (supposing a body weight of 60 kg), approximately 1.0 to 500 mg of the antibiotic, preferably approximately 5.0 to 300 mg, or more preferably approximately 5.0 to 200 mg is administered daily. When administering parenterally, although the dosage of the antibiotic varies with the administration subject, the target disease and the like, for instance, when a tetracycline-type antibiotic is administered in injectable form to a normal adult (supposing a body weight of 60 kg), it is convenient to administer by venous injection approximately 0.1 to 300 mg, preferably approximately 1 to 200 mg, or more preferably approximately 10 to 100 mg of the antibiotic daily. In the case of other animals, it is possible to administer an amount converted into per 60 kg body weight.

The composition of the present invention is used in combination with an antibiotic (for instance, tetracycline-type antibiotic). In one embodiment, the composition of the present invention contains a further antibiotic. In another embodiment, the composition of the present invention is used by being administered into a cell or a subject simultaneously with the antibiotic or before or after administration of the antibiotic.

5. Kit the Present Invention

In addition, in one embodiment, the present invention provides a kit containing the fusion protein of the present invention, a kit containing a polynucleotide encoding the fusion protein the present invention, a kit containing an expression vector containing a polynucleotide encoding the fusion protein the present invention, as well as a kit containing an expression vector containing the polynucleotide encoding the fusion protein of the present invention and a polynucleotide for controlling the expression of the polynucleotide. In addition, the present invention provides a kit containing the composition of the present invention described above in 4.

Normally, the kit of the present invention further contains an antibiotic (for instance, tetracycline-type antibiotic). The kit of the present invention may be used, for instance, for introducing in vitro or ex vivo an expression vector containing the polynucleotide encoding the fusion protein of the present invention into a cell to create and select a transfected cell. In addition, the kit of the present invention may contain a buffering solution, a syringe, a vial, and the like, which are necessary to the desired formulation for in vivo use. In addition, the kit of the present invention may further contain instructions by the manufacturer describing the employment method and/or usage precaution, and the like.

6. Method for Controlling Protein Degradation by an Antibiotic of the Present Invention In one embodiment, the present invention provides a method for controlling protein degradation by an antibiotic (for instance, tetracycline-type antibiotic) that can be introduced into the interior of a cell. This method includes either step (A) or (B) described below:
(A) Step of expressing inside a cell or inside an organism a polynucleotide encoding a fusion protein containing a mutant protein of a protein that binds to the antibiotic and a target protein fused thereto, in the presence or in the absence of the antibiotic.
(B) Step of using inside a cell or inside an organism a fusion protein containing a mutant protein of a protein that binds to the antibiotic and a target protein fused thereto, in the presence or in the absence of the antibiotic.

In a preferred embodiment, the antibiotic is a tetracycline-type antibiotic and the protein that binds to the antibiotic is the repressor protein of the antibiotic.

One preferred embodiment of the present invention described above is a method for controlling protein degradation by a tetracycline-type antibiotic. This method includes either step (A) or (B) described below:
(A) Step of expressing inside a cell or inside an organism a polynucleotide encoding a fusion protein containing a mutant TetR protein and a target protein fused thereto, in the presence or in the absence of the tetracycline-type antibiotic.
(B) Step of using inside a cell or inside an organism a fusion protein containing a mutant TetR protein and a target protein fused thereto, in the presence or in the absence of the tetracycline-type antibiotic.

In a further other embodiment, the present invention further provides a method for controlling the transcription of a gene encoding a target protein by a antibiotic (for instance, tetracycline-type antibiotic) that can be introduced into the interior of a cell, and controlling the degradation of the target protein as the expression product of the gene. This method contains the step described below:
(C) Step of using an expression vector containing expressibly a polynucleotide encoding a fusion protein containing a mutant protein of a protein that binds to the antibiotic and a target protein fused thereto, as well as a polynucleotide for controlling the transcription of the polynucleotide, to express inside a cell or inside an organism the polynucleotide encoding the fusion protein in the presence or in the absence of the antibiotic.

In the method of the present invention described above, (i) the polynucleotide encoding the fusion protein containing the mutant protein that binds to the antibiotic and the target protein fused thereto and (ii) the polynucleotide for controlling the transcription of the polynucleotide may each be contained expressibly in different expression vectors.

For instance, for experimental purposes or for the purpose of diagnostics, prevention and treatment of a disease, the method of the present invention described above may be used in order to introduce, in vitro or ex vivo, a gene encoding the fusion protein of the present invention into the interior of a cell to express the gene in the presence or in the absence of an antibiotic (for instance, tetracycline-type antibiotic), or, in order to introduce, in vivo, a gene encoding the fusion protein of the present invention into the interior of a cell of a subject or of a tissue or organ containing such a cell to express the gene there in the presence or in the absence of an antibiotic (for instance, tetracycline-type antibiotic). The introduction of the gene (or polynucleotide) encoding the fusion protein of the present invention into the interior of a cell may be carried out according to an analogous method to that already described above in 3.

In addition, for instance, for experimental purposes or for the purpose of diagnostics, prevention and treatment of a disease, the method of the present invention described above may be used in order to use, in vitro or ex vivo, the fusion protein of the present invention inside a cell in the presence or in an absence antibiotic (for instance, tetracycline-type antibiotic), or, in order to use, in vivo, the fusion protein of the present invention inside the cell of a subject or of a tissue or organ containing such a cell in the presence or in the absence of an antibiotic (for instance, tetracycline-type antibiotic).

In the method of the present invention, although the fusion protein or the gene encoding the fusion protein can be administered or brought to contact directly with a cell or the tissue of a subject, or the like, preferably, the formulation may be together with an appropriate carrier, diluent or excipient, and the like to be introduced into a cell or inside an organism as described above in 4. In the method described above, before, at the same time as or after a fusion protein or the gene encoding the fusion protein is administered or provided into the interior of a cell or of an organism, the antibiotic (for instance, tetracycline-type antibiotic) may be administered or provided into the interior of the cell or of the organism described above. In the method, protein degradation may be regulated by regulating (increasing and decreasing) the concentration (inside a cell or a tissue) of the antibiotic (for instance, tetracycline-type antibiotic).

The present invention will be described more concretely using examples; however, the scope of the present invention is not to be limited by these examples.

EXAMPLES

Example 1

Preparation and verification of stability of wild-type TetR-EGFP and mutant TetR-EGFP 1. Materials and Methods
A. Preparation of cDNA All of or any two mutations in combination from three types of mutations, which substitute aspartic acid at the $95^{th}$ position with asparagine, leucine at the $101^{st}$ position with serine and glycine at the $102^{nd}$ position with aspartic acid, were introduced into the tetracycline repressor (TetR), which is an *Escherichia coli* protein that binds to the antibiotic tetracycline (Tet). The procedure was as follows:

(Procedure)

An oligonucleotide encoding an amino acid sequence containing the amino acid substitution to be introduced was synthesized, and this was used to prepare a DNA fragment containing a mutation by PCR reaction. This fragment was used to replace the corresponding site on the DNA encoding the wild-type protein to introduce the mutation.

Next, cDNAs encoding TetR-EGFP in which wild-type TetR gene and mutation-introduced TetR gene, respectively, are fused with green fluorescent protein (EGFP) were created. The procedure was as follows.

(Procedure)

An oligo-DNA was synthesized, having a base sequence in which the termination codon has been substituted so as to encode another amino acid instead of the termination codon in the TetR gene, and downstream thereof, a sequence that is recognized and cut by a restriction enzyme; this was used to carry out a PCR reaction to prepare a DNA fragment encoding TetR with no termination codon, and this was substituted with the corresponding site on the DNA encoding the wild-type gene. Then, the DNA was cut by a restriction enzyme and ligated with the upstream side of a DNA fragment encoding EGFP in such a way that the translation open reading frames for protein synthesis match (FIG. 1A).

B. Preparation of Gene Expression Vector

The cDNA prepared as described above was integrated into the gene expression vector "pEB6CAG" developed by the present inventors and collaborators, which is replicated/maintained stably in human cells. The constructed expression vector DNA was prepared in large amounts from *Escherichia coli* using a commercially available DNA purification kit.

C. Preparation and Selection of Transfected Cells

Using a commercially available lipofection reagent, this DNA was introduced into the human cell line HEp-2, which was cultured for four days in the presence of 1.5 mg/ml G418, and only those cells in which DNA were introduced were selected. The cells were recovered by trypsin treatment and the ratio of fluorescence-positive cells and the intensity of fluorescence of individual cell were analyzed with a flow cytometer (BD FACSCalibur).

2. Results
A. Measurement of the Intensity of Fluorescence by Flow Cytometer

FIGS. 1B to D are graphs showing the results when the stability of wild-type TetR-EGFP and mutant TetR-EGFP was examined using a flow cytometer.

With cells expressing wild-type TetR-EGFP, EGFP-derived fluorescence was observed in 90% or more of the cells, and with cells expressing mutant TetR-EGFP, only extremely weak fluorescence could be observed in about 10 to 20% of the cells (FIG. 1B).

When these cells were cultured in the presence of 100 μg/ml of the proteasome inhibitor MG132 for 12 hours, although no major change in the intensity of fluorescence was observed with the cells expressing wild-type TetR-EGFP, a remarkable enhancement of fluorescence was observed with the cells expressing mutant TetR-EGFP (FIG. 1C). From this, degradation of the mutant TetR-EGFP protein inside the cells by the proteasome was found to be the cause for the observation of only little fluorescence.

In addition, when this cell was cultured for four days by adding 1.5 mg/ml of doxycycline, although no change was observed with wild-type TetR-EGFP, a remarkable enhancement of fluorescence was observed with cells expressing the mutant, which was greater than when MG132 was added (FIG. 1D). Note that the TetR used here was one into which all three of the three types of mutations described above were introduced.

B. Observation by Inverted Microscope

Figure 2:
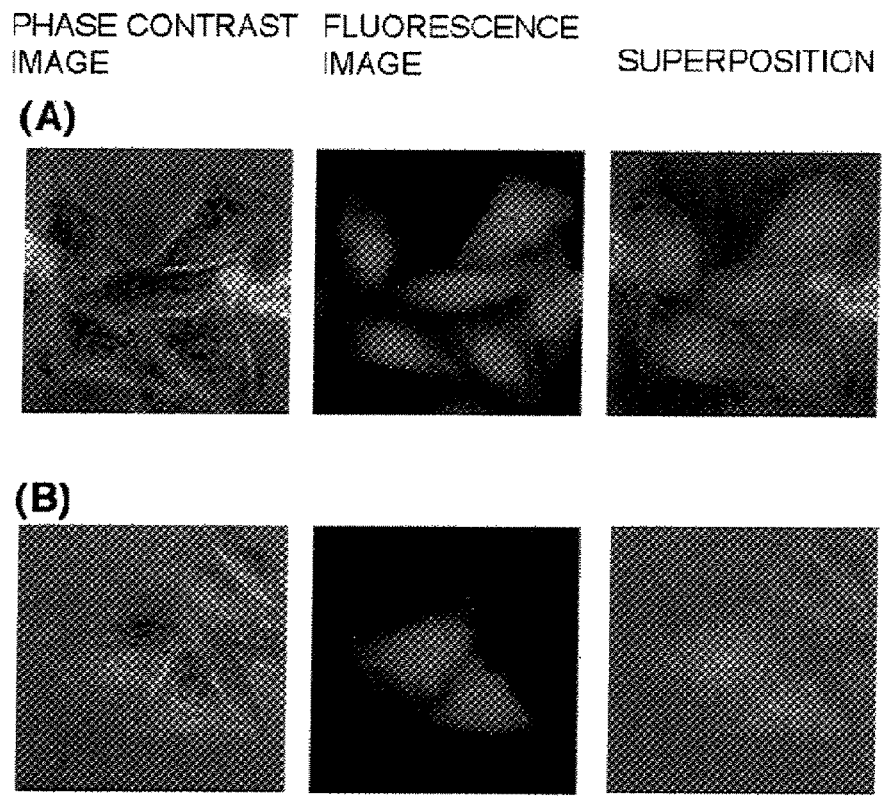
FIG. 2 shows photographs showing fluorescence changes, when cells expressing mutant TetR-EGFP were cultured in the presence of doxycycline.

FIG. 2A is an inverted microscope photograph of the cell described above. As is shown, although green fluorescence was observed over the entirety of the cell, the fluorescence was biased particularly to the nucleus (FIG. 2A). Since TetR is a DNA binding protein, this was presumed to be due to the presence of the protein biased to the nucleus by binding to the genomic DNA inside the human cell. It was predicted that this might become an issue in some cases when application to a general purpose is attempted. Consequently, in order to deactivate the DNA binding capability, a further mutation to substitute arginine at the $28^{th}$ position with glutamine was introduced.

FIG. 2B is a photograph showing the results of fluorescence microscope observations carried out using a TetR-EGFP mutant with the R28Q mutation added. As shown, localization of fluorescence to the nucleus was solved, fluorescence is observed uniformly inside the cell and the border between the nucleus and the cytoplasm became indistinct. In addition, with this mutation, the extent of doxycycline-dependent fluorescence enhancement was also maintained (FIG. 2B).

C. Correlation Between Doxycycline Concentration and Intensity of fluorescence

Figure 3:
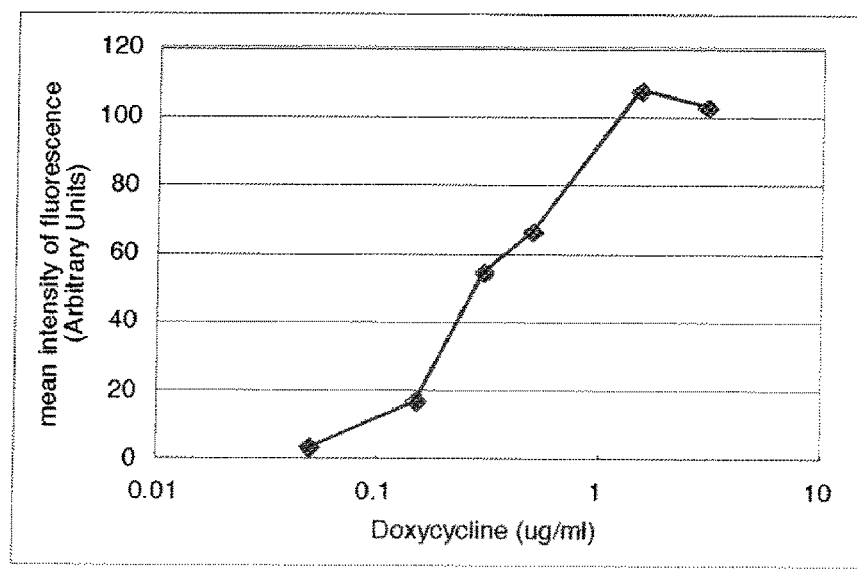
FIG. 3 is a graph showing the results of intensity of fluorescence analyzed with a flow cytometer for cells expressing mutant TetR-EGFP by addition of various concentrations of doxycycline.

In order to analyze the correlation between doxycycline concentration and intensity of fluorescence, the intensity of fluorescence in states where various concentrations of doxycycline were added was analyzed with a flow cytometer. FIG. 3 shows the results. As shown, enhancement of fluorescence started to be observed at concentrations of 0.05 μg/ml or more and the maximum intensity of fluorescence was reached when the concentration was 1.5 μg/ml.

Figure 4:
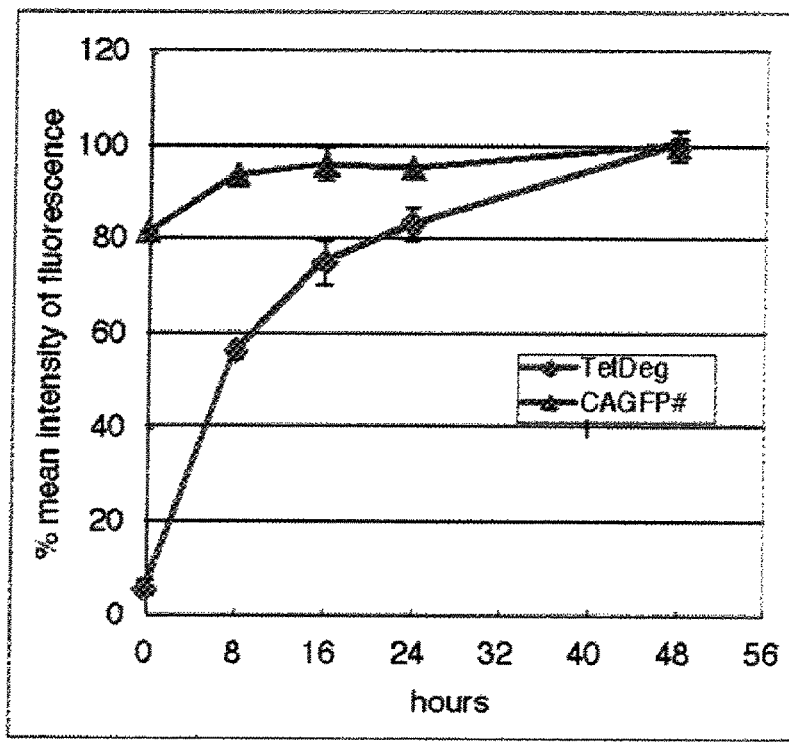
FIG. 4 (A) is a graph showing the changes in the intensity of fluorescence after addition of doxycycline in cells expressing mutant TetR-EGFP compared to cells simply expressing EGFP only.
Figure 4:
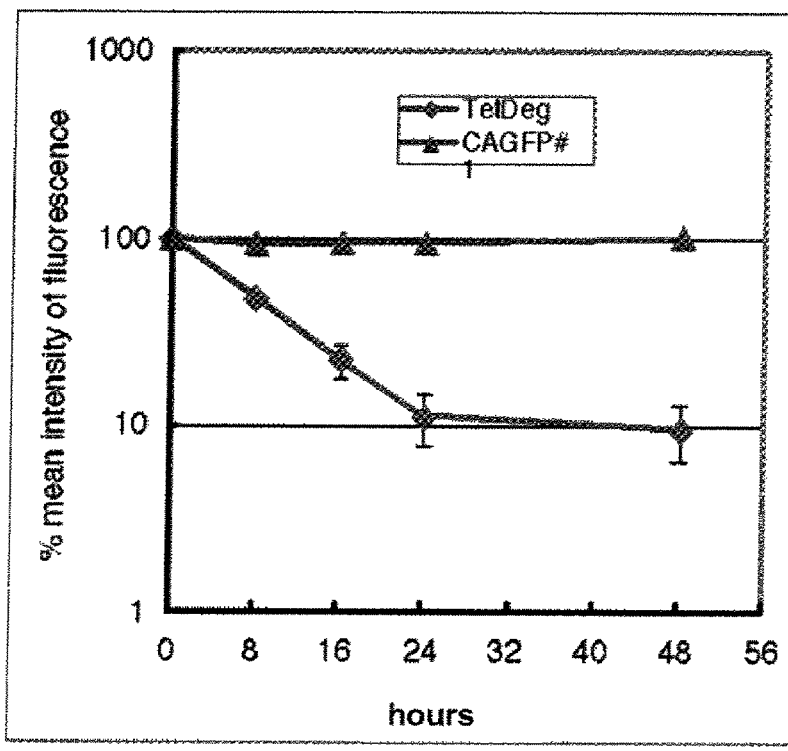

D. Correlation Between Time Elapsed after Addition of Doxycycline and Intensity of Fluorescence In order to analyze variation over time after addition of doxycycline, intensity of fluorescence was measured every eight hours after addition of 1.5 μg/ml of doxycycline. FIG. 4A shows the results. As shown, compared to cells transfected with a vector simply expressing EGFP, cells transfected with a vector expressing mutant TetR-EGFP demonstrated a sudden fluorescence enhancement the first eight hours, and the fluorescence had almost reached equilibrium after 24 hours (FIG. 4A). Conversely, in order to observe the time course after removal of doxycycline, after treatment with 1.5 μg/ml of doxycycline for four days, an exchange to a MEM culture medium containing no doxycycline was performed and the intensity of fluorescence was measured every eight hours. The results are shown in FIG. 4B. As shown, the half life was eight hours, and fluorescence disappeared almost completely after 24 hours (FIG. 4B).

Example 2

Evaluation of the Capabilities of the Protein Degradation Control System of the Present Invention In Vivo 1. Evaluation in Trasgenic Mouse A transgenic mouse was created in order to analyze whether or not the behavior of doxycycline was detectable as fluorescence in a live individual animal using this protein degradation control system.

A cDNA of TetR-EGFP into which the R28Q, D95N, L101S and G102D mutations were introduced was linked downstream of the CAG promoter known to facilitate the expression of a transgene systemically in mouse, and an IRES sequence and a cDNA that is capable of expressing a tandem dimer of fluorescent protein DsRed were placed further downstream, sandwiching the IRES sequence by the cDNAs. Since it was predicted that the intensity of green fluorescence varies due to the TetR-EGFP protein which undergoes degradation control by the presence or absence of doxycycline while the red fluorescence of DsRed would always be constant, it was expected that the intensity of expression in each of the various organs would be monitored by the red fluorescence and that the variation in the intensity of green fluorescence due to the behavior of doxycycline would be standardized and quantified by taking the ratio of red and green fluorescence intensities.

Consequently, DNA prepared in large amounts was injected into mouse fertilized eggs, then, returned into a pseudo-pregnant mouse, and from among the born mouse pups, one having the transgene was selected and bred.

Figure 5:
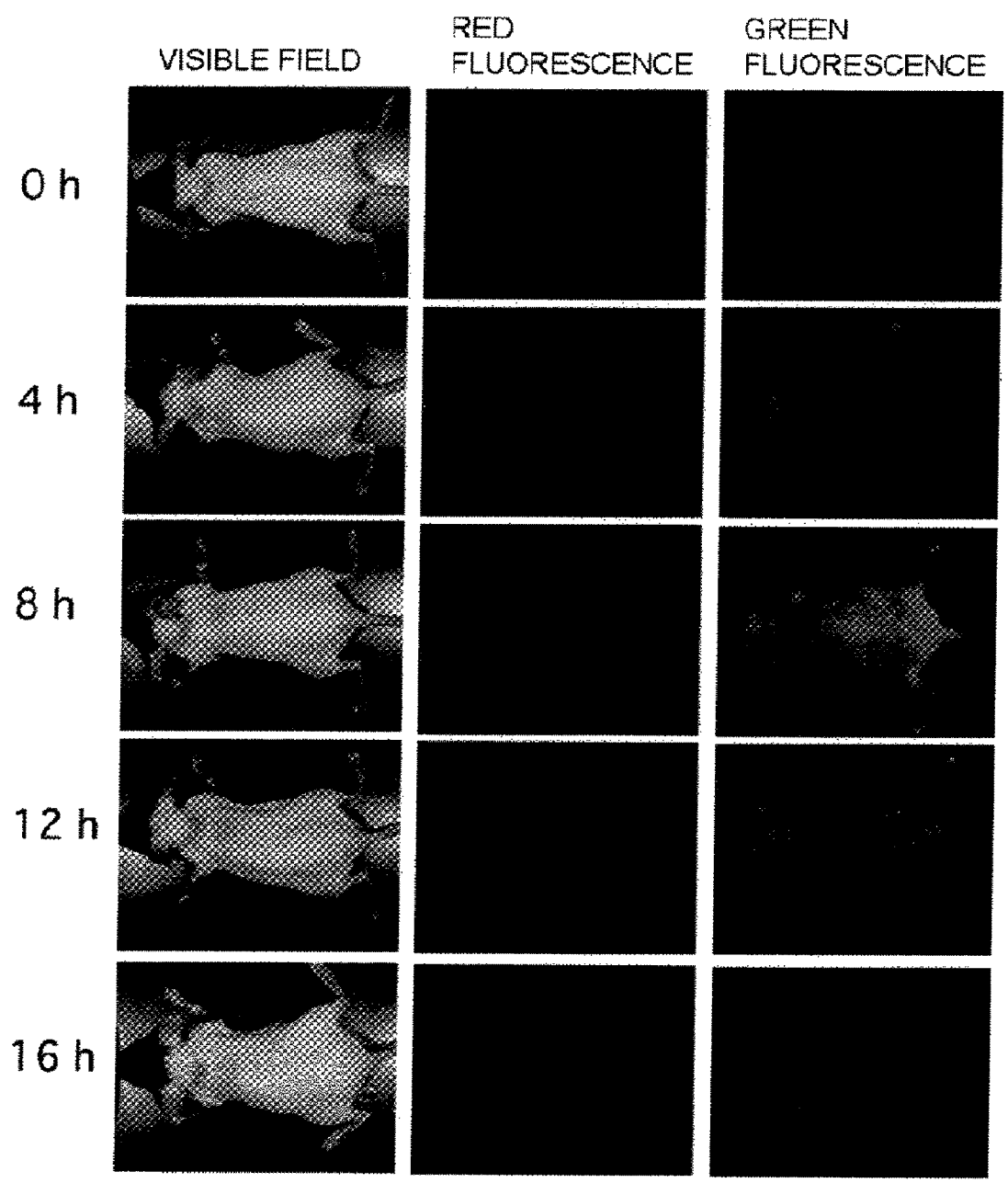
FIG. 5 shows photographs showing the results when the fluorescence in a mouse injected with and expressing a vector that has the genes for mutant TetR-EGFP and DsRed integrated was observed over a time course using an inverted microscope.
Figure 6:
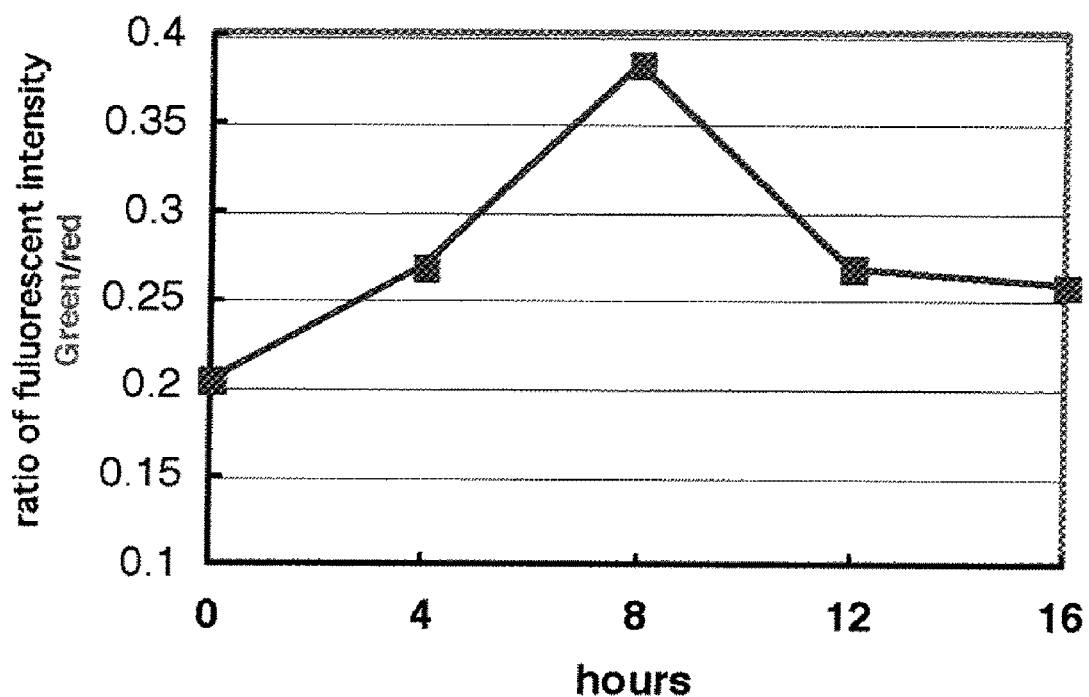
FIG. 6 is a graph showing the changes over time of the intensity of fluorescence in the experiment of FIG. 5.

As expected, in this mouse, red fluorescence was always observed, and furthermore when doxycycline was administered into the peritoneal cavity, enhancement of green fluorescence occurred systemically after eight hours (FIG. 5). When the ratio between the red and green fluorescence intensities was graphed, the intensity of green fluorescence was found to become maximum at the eighth hour and decay thereafter (FIG. 6).

2. Evaluation in Zebrafish

In order to verify whether or not a similar degradation control occurs in other animal species, an mRNA encoding TetR-EGFP into which the R28Q, D95N, L101S and G102D mutations were introduced was synthesized with a commercially available kit and injection was carried out into a zebrafish fertilized egg.

Figure 7:
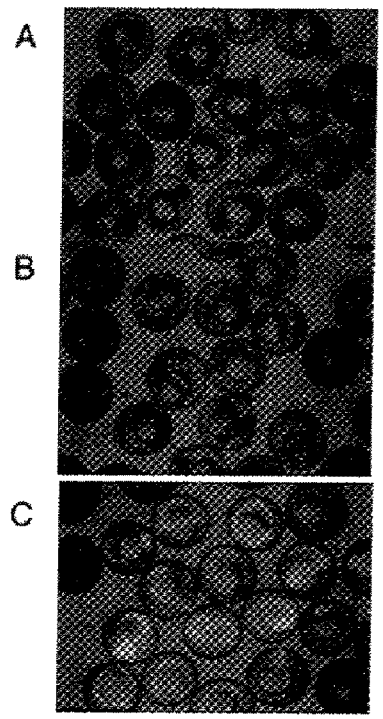
FIG. 7 shows photographs showing the results when an mRNA encoding a mutant TetR-EGFP was injected into zebrafish fertilized eggs and the fluorescence was observed in the presence or in the absence of doxycycline using an inverted microscope.

Although no green fluorescence was detected when no doxycycline was added, when 1.5 μg/ml of doxycycline was added, a weak fluorescence was observed 24 hours later in 40% of the eggs, and when 15 μg/ml was added, extremely strong fluorescence was observed in 100% of the eggs (FIG. 7). As described above, it was demonstrated that a degradation control system similar to that used in mouse can also be used in fish.

Example 3

Quantitative Analysis of Protein Expressed Using the Gene Expression Regulation and/or Protein Degradation Regulation System of the Present Invention (1)

A. Preparation of Gene Expression Vectors

A cDNA was integrated into the constitutive gene expression vector "pEB6CAG" or the vector "pOSTet15" enabling transcription-regulated expression through doxycycline, which the present inventors developed by applying the methods in Japanese National-phase PCT Laid-Open Patent Publication No. 2003-515314 (the entirety of which is incorporated herein by reference). The cDNA to be expressed integrates a simple fluorescent protein EGFP, or eTetREGFP or hTetREGFP, which degradation control is enabled by doxycycline. According to this, the following six vectors were constructed: 1) "pEB6CAG-EGFP", which expresses constitutively with no control at all, 2) "pOSTet15-EGFP", for which control is possible only at the transcription level, 3) "pEB6CAG-eTetREGFP" and "pEB6CAG-hTetREGFP", for which control is possible only at the protein degradation level and 4) "pOSTet15-eTetREGFP" and "pOSTet15-hTetREGFP", for which dual-control at the transcription level and the protein degradation level is possible. The constructed expression vector DNA was prepared in large amounts from *Escherichia coli* using a commercially available DNA purification kit.

B. Preparation and Selection of Transfected Cell

Using a commercially available lipofection reagent, this DNA was introduced into the human cell line HEp-2, the cell line was cultured for four days in the presence of 1.5 mg/ml G418, and only cells with the DNA introduced were selected. These cells were subjected to a flow cytometer and the intensity of fluorescence by EGFP was measured cell by cell to determine the average fluorescence intensity thereof.

Results

Figure 8:
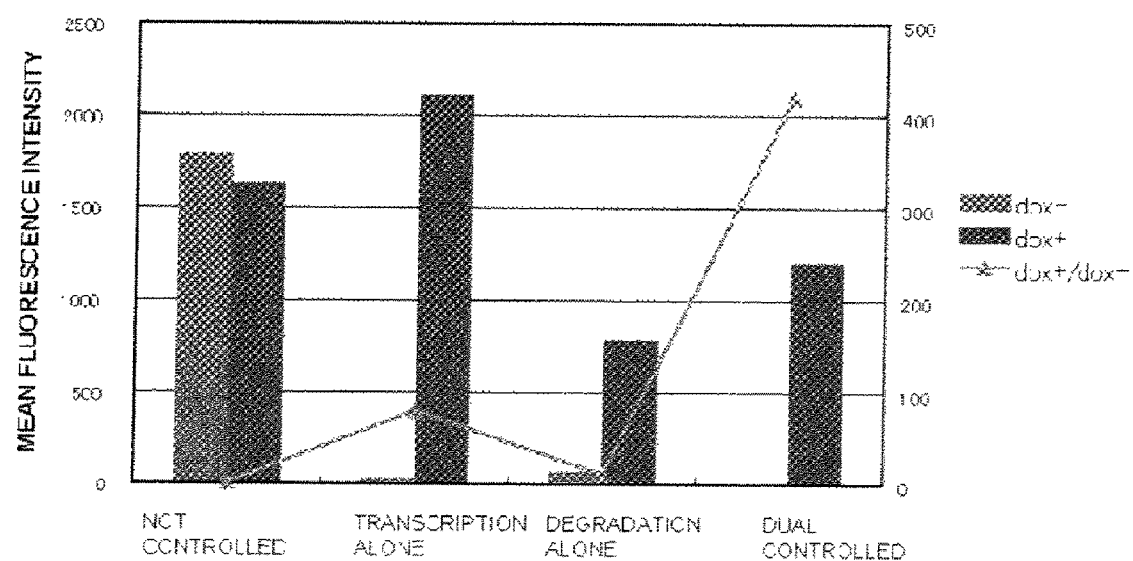
FIG. 8 is a graph showing the control effects on the quantity of intracellular protein when the system of the present invention was used to control gene transcription and/or protein degradation.

As shown in FIG. 8, when neither transcription nor protein degradation control is applied, strong fluorescence was detected regardless of the presence or absence of doxycycline. If expression control was applied by transcription alone or degradation alone, the intensity of fluorescence when no doxycycline was added was weaker, and although a given control effect was observed, fluorescence was still detected in many cells. This means that expression inhibition is insufficient with a single control.

Meanwhile, when a dual-control was applied, almost no fluorescence was detected when no doxycycline was added, furthermore, since a strong fluorescence was detected when doxycycline was added here, in contrast to the induction ratio thereof of several tens of times that for a single control, a remarkable induction of 400 times or greater was observed. Moreover, it was found that control at a lower expression level was possible when eTetR in which the cDNA sequence was still *Escherichia coli*-derived was used, and control at a higher expression level was possible with hTetR in which the cDNA sequence was converted into codons used at high frequency in human. From this, it was demonstrated that eTetR and hTetR can be used separately according to the type of the objective protein to be introduced/expressed and the expression level aimed for.

From the above results, it was demonstrated that even in cases where stringent enough expression control is difficult with the transcription control by doxycycline of the prior art alone, extremely stringent gene expression control can be realized by combination with the control of protein degradation of the present invention.

Example 4

Quantitative Analysis of Protein Expressed Using the Gene Expression Regulation and/or Protein Degradation Regulation System of the Present Invention (2)

cDNAs encoding DTA-EGFP, in which the diphtheria-derived toxin protein diphtheria toxin A (DTA) gene which demonstrates strong toxicity against human cells, fused with a green fluorescent protein (EGFP), and eTetR-DTA-EGFP and hTetR-DTA-EGFP, in which the foregoing DTA-EGFP was further fused with mutant TetR, were prepared to perform experiments to control gene transcription. The procedure was as follows:

(Procedure)

A. Preparation of TetR-DTA-EGFP cDNA fragment encoding DTA was prepared by excision from an existing pMC1 DT-3 vector with restriction enzymes BamHI-DraI. This was inserted into a cDNA in which the TetR portion of the mutant TetR-EGFP gene described above was removed by restriction enzymes BglII-SmaI to create a cDNA encoding DTA-EGFP. In addition, eTetR-DTA-EGFP and hTetR-DTA-EGFP were created by inserting the cDNA fragment encoding DTA between TetR and EGFP of the TetR-EGFP gene, using the restriction enzyme BamHI.

B. Preparation of Gene Expression Vectors

The cDNA prepared as described above was integrated into the constitutive gene expression vector "pEB6CAG" or the vector "pOSTet15" enabling regulated expression through doxycycline, which the present inventors developed by applying the methods in Patent Laid-open Publication No. 2003-515314. According to this, the following six vectors were constructed: 1) "pOSTet15-eTetRDTAEGFP" and "pOSTet15-hTetRDTAEGFP", which enable dual-control at the transcription level and the protein degradation level, 2) "pOSTet15-DTAEGFP", which enables control at the transcription level, 3) "pEB6CAG-eTetRDTAEGFP" and "pEB6CAG-hTetRDTAEGFP", which enable control only at the protein degradation level and 4) "pEB6CAG-DTAEGFP", which expresses constitutively with no control at all. In addition to these, "pOSTet15-eTetREGFP" and "pOSTet15-hTetREGFP", which have no DTA and demonstrate no cytotoxicity, were also constructed for the comparative experiments. The constructed expression vector DNA was prepared in large amounts from *Escherichia coli* using a commercially available DNA purification kit.

C. Preparation and Selection of Transfected Cell

Using a commercially available lipofection reagent, this DNA was introduced into the human cell line HEp-2, the cell line was cultured for four days in the presence of 1.5 mg/ml G418, and only cells with the DNA introduced were selected. At this time, the surviving cell count was measured. In addition, EGFP fluorescence observation was carried out for confirmation of gene introduction.

Results

Figure 9:
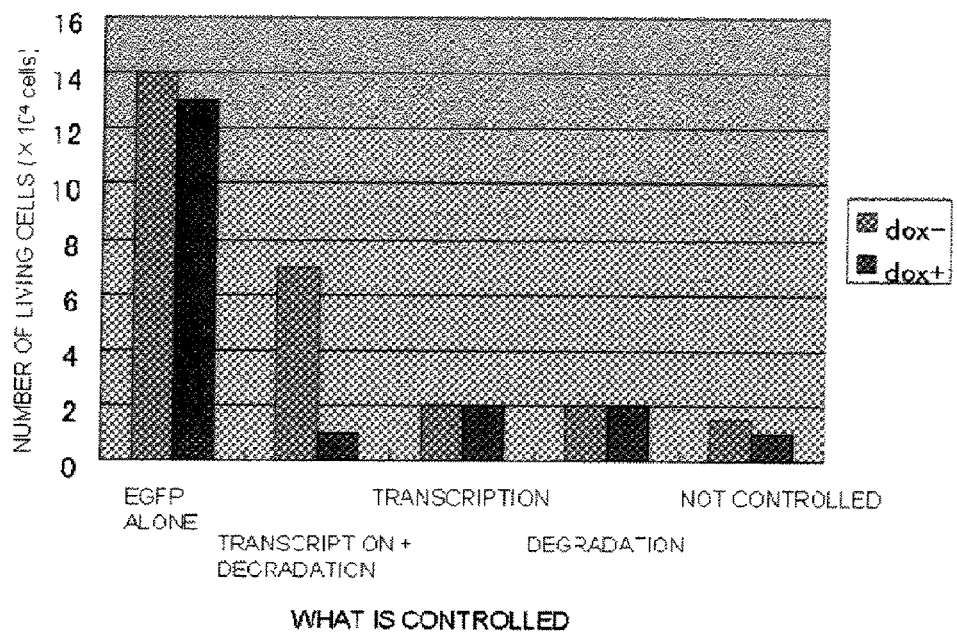
FIG. 9 is a graph showing the results when viable cell counts were compared between the control of transcription of a toxin gene by doxycycline only in a cell and the expression control of the toxin gene using the protein degradation control method of the present invention, in the presence and in the absence of doxycycline.

As shown in FIG. 9, similarly to when there was no expression control, when control was applied with either transcription or protein degradation alone, almost all the cells killed even when expression was inhibited with no doxycycline added. This means that inhibition of expression being insufficient with a single control, the cells were killed due to the high toxicity of DTA even with an expression leakage at low level.

Meanwhile, if a dual-control was applied, the cells were killed even without addition of doxycycline when hTetR was used, similarly to the cases of a single control. On the other hand, when eTetR was used, although the cell count when doxycycline was not added has become lower than when a gene without toxicity was introduced, a sufficient number of cells were shown to have survived due to sufficient expression inhibition of the toxin gene. In addition, it became also clear that when doxycycline was added here the toxin gene was expressed, killing the cells.

From the above results, it was demonstrated that even in cases where stringent enough expression control is difficult with the transcription control by doxycycline of the prior art alone, extremely stringent gene expression control can be realized by combination with the control of protein degradation of the present invention. In particular, it became also clear that if an expression control is desired, of a gene which influence exerted on cells is large even with a slight expression, such as the diphtheria toxin of this time, the most stringent expression inhibition can be realized by selecting eTetR.

Example 5

Figure 10:
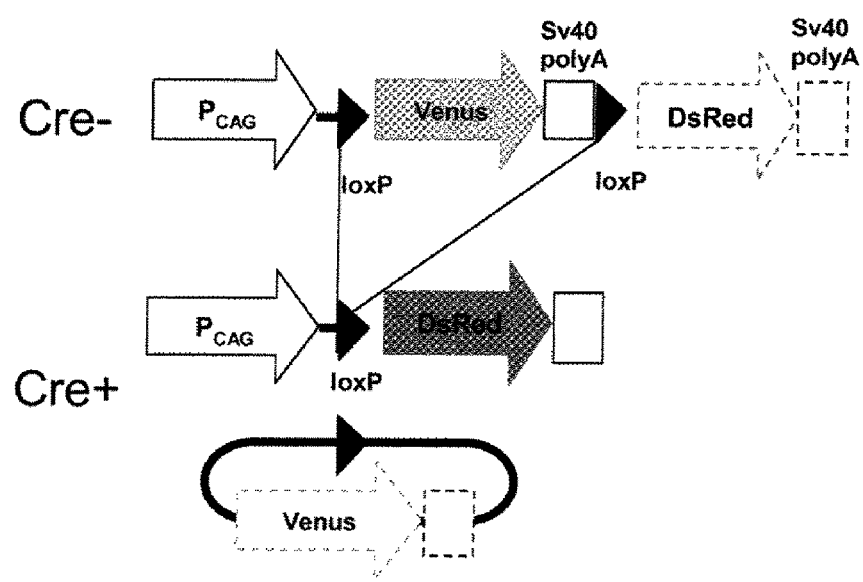
FIG. 10 is a schematic showing the recombination reporter vector pEB6CAG-Venus-lox-R1.

Regulation of Expression of a Target Gene by the Dual Control System Containing Gene Expression Regulation and Protein Degradation Regulation of the Present Invention A. Preparation of Gene Expression Vectors As vectors to control the expression of the lambda phage Cre protein, three types of vectors were constructed for: control by protein degradation only, control by transcription only and dual control. In addition, in so doing, similarly to hTetR, in which the codons of TetR were modified, was used in Examples 3 and 4, when the cre gene with the normal base sequence and hCre (SEQ ID: 3) in which, in order to raise the translation efficiency in mammalian cells, the types of codons were modified to alter the base sequence only, keeping the amino acid sequence as-is, were compared, since hCre was confirmed to have a higher recombination efficiency overall, hCre was used in the present example. Three types of vectors were constructed, "pEB6CAG-TetRhCre", which enables control by degradation alone, and created by turning the hCre cDNA into TetRhCre which enables degradation control by doxycycline, and which was then integrated into the constitutive gene expression vector "pEB6CAG" described above; "pOSTet15-hCre", which enables control by transcription alone and was created by integrating hCre cDNA into "pOSTet15": "pOSTet15-TetRhCre", which enables dual control and created by integrating TetRhCre into "pOSTet15". In addition to these, as a monitoring vector for confirming the DNA recombination effect by the Cre protein, a recombination reporter vector in which the yellow fluorescent protein Venus was flanked by loxP sequences and the red fluorescent protein DsRed1 was placed downstream thereof, "pEB6CAG-Venus-lox-R1-SRZ" (FIG. 10), was also constructed. By introducing this at the same time as any Cre control vector described above into a cell, while a cell in which no Cre expression is observed emits a yellow fluorescence, if a Cre-mediated recombination between loxP occurs, the Venus cDNA is eliminated and the expression of DsRed1 starts, causing red fluorescence to be emitted. The expression effect of Cre can be detected simply from this change in fluorescence wavelength (FIG. 10).

The constructed expression vector DNA was prepared in large amounts from *Escherichia coli* using a commercially available DNA purification kit B. Preparation and Selection of Transfected Cell Using a commercially available lipofection reagent, this DNA was introduced into the human cell line HEp-2, the cell line was cultured for four days in the presence of 1.5 mg/ml G418 and 0.1 mg/ml zeocin, and only cells with the two species of DNA introduced were selected. Fluorescences at two wavelengths, yellow and red, were measured with a flow cytometer.

Results

Figure 11:
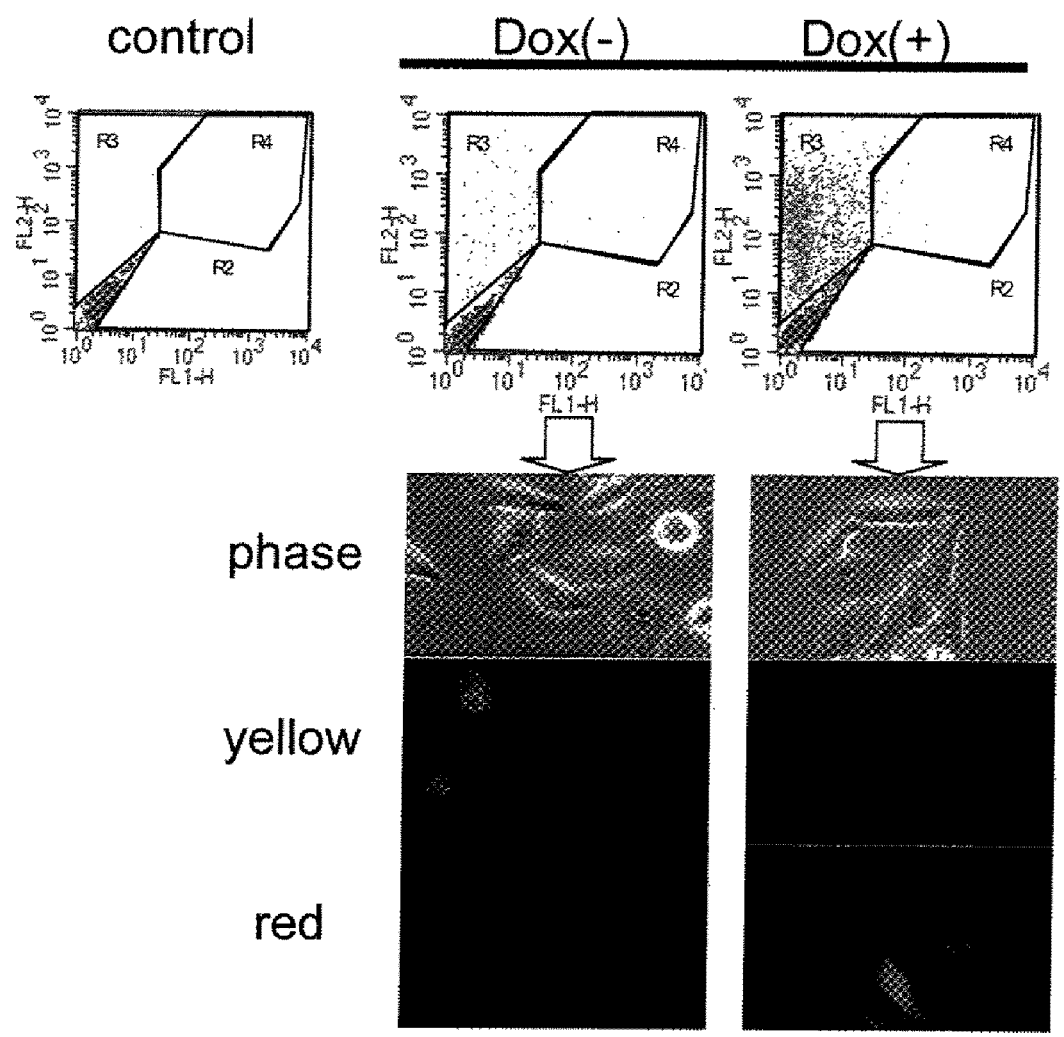
FIG. 11 is a figure showing the control effect on the amount of intracellular Cre protein by the dual control of gene expression and protein degradation using the recombination reporter vector pEB6CAG-Venus-lox-R1.

As shown in FIG. 11, when no doxycycline was added, most of the cells displayed yellow fluorescence, and those cells simultaneously displaying red fluorescence were on the order of 5%. On the other hand, when 1 mg/ml of doxycycline was added, 60% of the cells displayed red fluorescence only, and by adding cells displaying both yellow and red, red fluorescence was detected in 70% or more of the cells; a recombination of the reporter vector by Cre was observed. In addition, even in cells emitting yellow fluorescence only, the fluorescence intensity thereof was considerably attenuated, suggesting that although DsRed1 was not correctly expressed, the recombination per se occurred.

Example 6

Control Efficiency Comparison Between Dual Control System and Protein Degradation Control System or Transcription Control System Next, comparison on the capabilities was performed, between when Cre protein expression regulation is carried out by protein degradation control alone and transcription control alone, and the dual control system of the present invention. After two vectors were introduced, three experiments were carried out: 1) one in which no doxycycline at all was added and was cultured for six days, 2) one in which 1.0 μg/ml of doxycycline was added only one day, thereafter, doxycycline was removed and was cultured for five days, and 3) one in which 1.0 μg/ml of doxycycline was added for three days, thereafter, doxycycline was removed and was cultured for three days.

Figure 17:
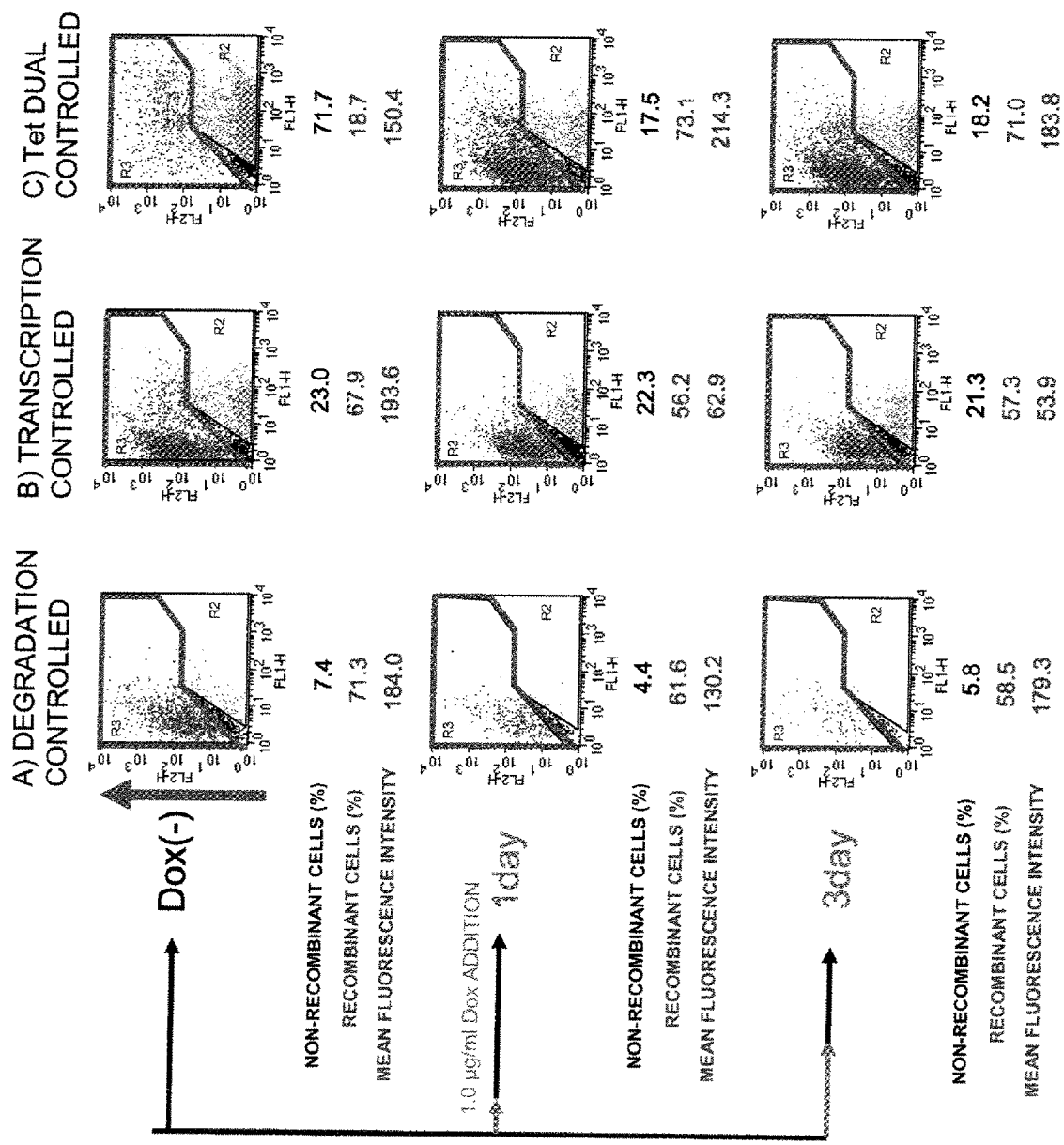
FIG. 17 shows graphs showing a comparison of control efficiency (or comparison of cell counts and intensity of fluorescence) between the case where regulation of the Cre protein expression was carried out by only protein degradation control with an antibiotic or by only transcription control with an antibiotic, and the case where regulation of the Cre protein expression was carried out by both protein degradation control and transcription control (dual control) with an antibiotic.

As shown in FIG. 17A, even if controlling the Cre protein by degradation alone was attempted, recombination of the reporter vector mediated by Cre had already occurred when doxycycline was not added, and there were 10% or less non-recombinant cells emitting yellow fluorescence were. Furthermore, when doxycycline was added here, cytotoxicity observed when Cre protein is expressed excessively in cells appeared, killing cells, and only few cells could be recovered. From this, it became clear that inhibition at uninduced time was insufficient with a control by protein degradation alone.

Next, as shown in FIG. 17B, also when controlling the Cre protein by transcription alone was attempted, although attenuated from the case of degradation alone, recombination of the reporter vector mediated by Cre was prominently observed already when doxycycline was not added, cells strongly emitting red fluorescence which indicates that recombination occurred were ⅔ or greater, meanwhile, non-recombinant cells emitting yellow fluorescence were 25% or less. Furthermore, when doxycycline was added here, cytotoxicity was observed similarly to the case of degradation control; in particular, since the cells having higher expression level and stronger red fluorescence were killed more, average intensity of red fluorescence of the cell group decreased remarkably, and the intensity of fluorescence decreased further when the doxycycline treatment time was extended. From the above, it was shown that although controlling by transcription alone is more stringent to some extent than controlling by degradation alone, it is insufficient as a method for controlling Cre protein expression.

Next, as shown in FIG. 17C, when the dual control system was used, 70% or more cells were cells emitting yellow fluorescence alone in which no recombination at all occurred, and the fluorescence intensity thereof was also large. However, when doxycycline was added here, 70% or more cells changed to red fluorescence even in a treatment of only one day; the recombination could be induced extremely efficiently. In addition, almost no decrease in cell count due to cytotoxicity, as observed in other cases, was observed even when treated for three days, and there was no major variation in the recombination efficiency per se from the one day only treatment.

From the above, it became clear that using the dual control system allows the enzymatic activity of a target protein to be inhibited stringently when no doxycycline is added, and furthermore, the enzymatic activity becomes detectable in most cells by doxycycline addition.

Example 7

Verification of Antibiotic Concentration Dependency of Tet Dual Control System Next, analyses were performed on the influence of the concentration of doxycycline exerted on recombination efficiency. Two species, the vector for Cre dual control and the recombination reporter vector described above, were introduced into a cell, and after selection over drugs the cells were treated for one day or three days with doxycycline at four concentration steps from 0.001 μg/ml to 1.0 μg/ml to examine recombination efficiency.

Figure 18:
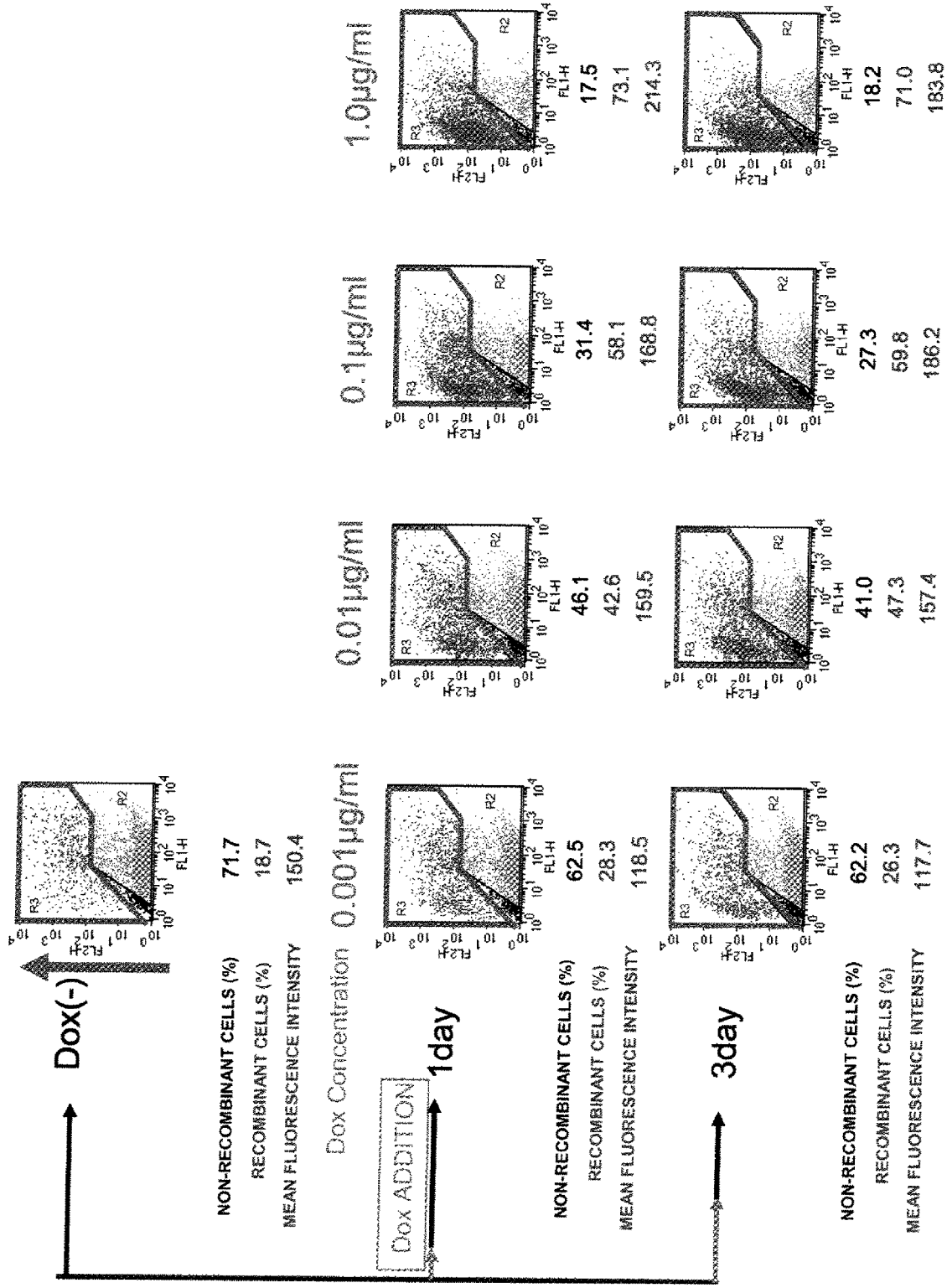
FIG. 18 shows graphs showing the antibiotic concentration dependency of the control efficiency of the system for the Tet-mediated transcription/degradation dual control of protein of the present invention.

As shown in FIG. 18, it was found that the efficiency of recombination rose concentration-dependently and that the concentration should be raised to 1.0 μg/ml in order to ensure that recombination occurs. Conversely, it was found that, since there was not so much variation in the efficiency even when the treatment time was tripled, 24 hours doxycycline treatment was sufficient, allowing a rather early induction to be realized.

Example 8

Method for Increasing Stringency of Control for the Control of Cre Gene Expression by the Dual Control System A. Preparation of Gene Expression Vectors As a method for controlling DNA recombination by the fusion protein of TetR and hCre more stringently in the vector "pOSTet15 TetRhCre", which has TetRhCre integrated in "pOSTet15" constructed in Example 5 and enables dual control, a method for altering the intracellular localization of the fusion protein was attempted. That is to say, A) in addition to the original TetRhCre fusion protein, B) one in which a nuclear localization signal (NLS) was added at the N-terminus, C) one in which a nuclear export sequence (NES) was added at the C-terminus and D) one in which placed were both NLS at the N-terminus and NES at the C-terminus, were constructed newly. These were introduced into cells similarly to Example 5 and the recombination efficiency was analyzed.

B. Preparation and Selection of Transfected Cell

These were introduced into cells similarly to Example 5 and the recombination efficiency was analyzed.

Results

Figure 19:
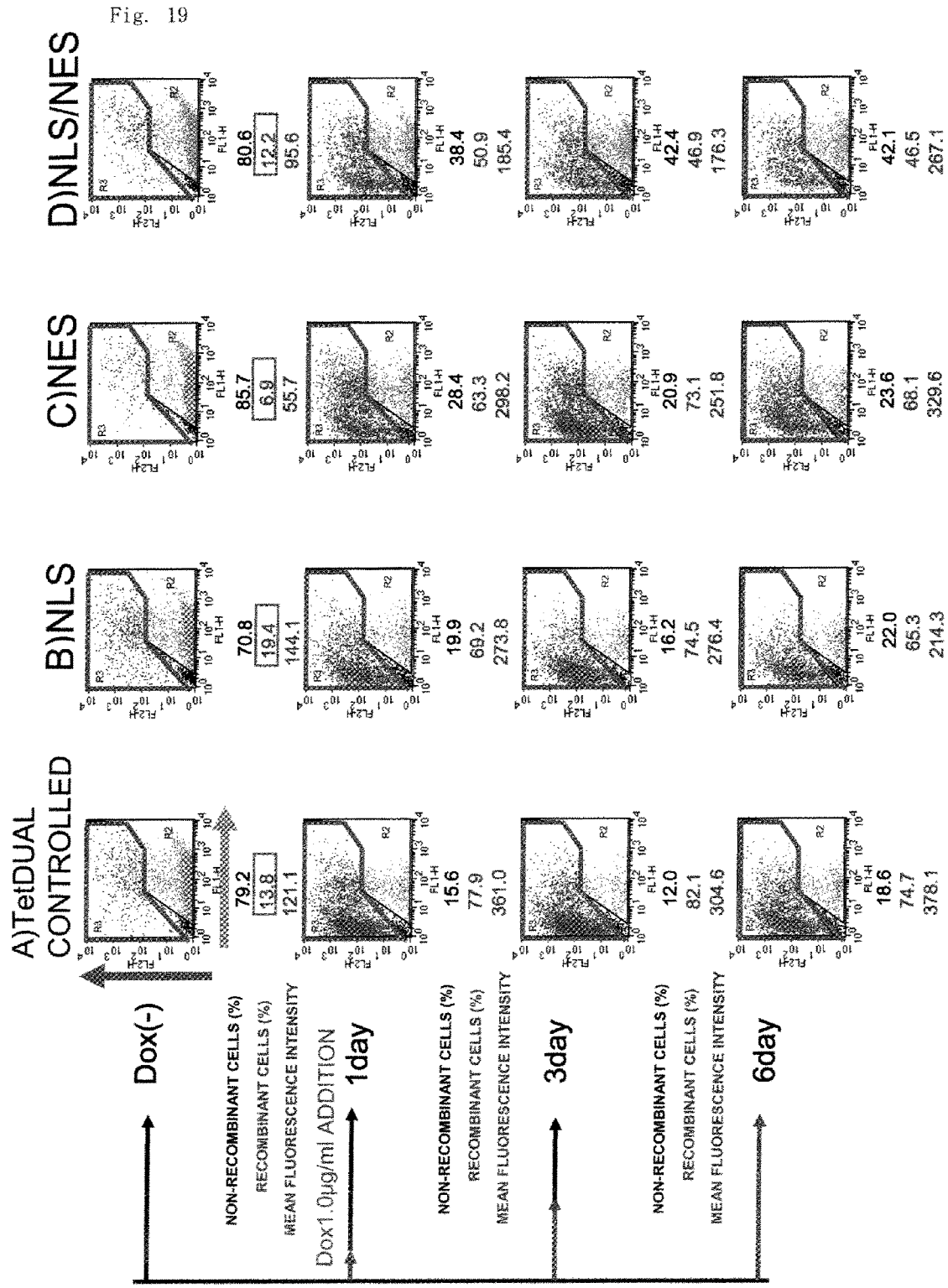
FIG. 19 is a graph showing the results of Cre expression analysis for the Tet dual control vector with improved recombination efficiency.

As shown in FIGS. 19A and B, it became clear that when Cre added with in general frequently used NLS to promote transport into the interior of the nucleus was used, the proportion of non-recombinant cells when no doxycycline was added decreased from 80% to 70%, moreover, the recombination efficiency when doxycycline was added was not different from that with nothing added, and thus there was an additional loss of stringency of expression control. On the other hand, as shown in FIG. 19C, it became clear that when NES was added to raise the rate of evacuation from the nucleus, cells that provoke recombination regardless of no addition of doxycycline was halved from 14% to 7%, and thus stringency was increased. In addition, it was shown that although the efficiency of induction of recombination by the addition of doxycycline also decreased slightly, it could be improved to some extent by extending the time of treatment to three days. As shown in FIG. 19D, when both NLS and NES were added, the control when no doxycycline was added did not increase and the recombination efficiency at addition time decreased widely, and thus the desirable capabilities were not exerted. From the above, it was shown that addition of NES is effective when controlling the expression of the Cre protein more stringently is desired.

INDUSTRIAL APPLICABILITY

The fusion protein of the present invention has the properties of being unstable and degraded quickly inside of a living animal cell in an isolated state while stabilizing and escaping degradation by binding to an antibiotic (for instance, tetracycline-type). In addition, according to the protein degradation control system of the present invention gene combined with transcription control (dual control system), it is possible to control the expression of a protein more stringently inside a living cell.

Consequently, the present invention can be used in such applications as of (1) to (4) below.

(1) Although the *Escherichia coli* tetracycline repressor (TetR) protein is stable inside a human cell, the mutant into which mutations have been introduced (for instance, at two locations or more) is rapidly degraded in a state without tetracycline-type antibiotic while it escapes degradation and accumulates inside the cell when Tet is added. Consequently, for instance, if a fusion protein of this mutant TetR protein and a target protein subject of a functional analysis is expressed by a cell, the amount of target protein inside the cell can be controlled by the amount of Tet added. This allows the influence exerted by the target protein on a cell or an individual organism to be analyzed experimentally.

(2) As a gene therapy, when an exogenous gene is introduced into a patient to improve the symptoms by the action of the protein, which is the gene product thereof, there is the danger that this protein becomes an antigen and triggers an unexpected adverse effect. Thus, for instance, if a fusion gene of a protein for the purpose of the treatment and a mutant TetR protein is introduced, the fusion protein amount, which is the product thereof, may be controlled by Tet, such that carrying out a treatment becomes possible while avoiding the adverse effects by administering Tet according to the situation of the patient. Consequently, the present invention is useful for applications in the medical field, or the like.

(3) If a mutant protein of a protein that binds to an antibiotic (for instance, mutant TetR) is expressed in a cell as a fusion protein with a detectable protein such as a fluorescent protein or a luminescent protein (example: luciferase), since the amount of fluorescence or the amount of luminescence varies with the amount of the antibiotic (for instance, Tet), the amount of antibiotic (for instance, Tet) in a living cell or in an individual organism can be detected and imaged. Consequently, the present invention is also useful in in vivo imaging of drugs, or the like.

(4) According to the composition, kit, system and method for controlling the expression of a target gene of the present invention, a regulation of the expression of a target gene becomes possible, such as, for instance, the expression of a target gene deemed necessary during a cycle in the process of cell differentiation is maintained for this period only and the expression of the gene is inhibited at the time point where it has become no longer necessary.

The invention claimed is:

1. A gene expression control system for controlling the expression of a target gene inside a cell in vitro or in a non-human transgenic animal by the presence or absence of a tetracycline antibiotic, comprising:
  (a) a cell
  (b) an expression vector that is introduced into the interior of said cell, and comprises expressibly
    (b1) a polynucleotide encoding a fusion protein of a mutant of a tetracycline repressor protein and a recombination enzyme, wherein said fusion protein mediates the recombination at a recombination sequence site, and is degraded inside said cell in the absence of said antibiotic,
    wherein said mutant has an amino acid sequence having at least two of the following mutations: substitution of aspartic acid at position 95 with asparagine, substitution of leucine at position 101 with serine and substitution of glycine at 102 with aspartic acid in the amino acid sequence of a wild-type tetracycline repressor protein encoded by SEQ ID NO: 2, and
    (b2) a polynucleotide to be introduced into the interior of said cell, encoding a protein that binds to the transcription control region of the polynucleotide in (b1) and controls the transcription of said polynucleotide, wherein the binding to said transcription control region is controlled by the presence or absence of said antibiotic,
  (c) an expression vector that is introduced into the interior of said cell, and comprises expressibly a target gene between and/or downstream of recombination sequences, and
  (d) a tetracycline antibiotic to be introduced into the interior of said cell,
    wherein the transcription of the polynucleotide in (b1) and the degradation of said fusion protein, which is the expression product of the polynucleotide in (b1), is controlled inside the cell by the presence or absence of the tetracycline antibiotic, and the expression of said target gene is controlled by the expressed amount of said fusion protein.

2. The system according to claim 1, wherein said recombination enzyme is at least one protein selected from the group consisting of:
  (a) Cre recombinase;
  (b) FLP recombinase;
  (c) phage phi 13 integrase;
  (d) phage R4 integrase;
  (e) phage TP901-1 integrase;
  (f) phage λ (lambda) integrase;
  (g) phage HK022 integrase;
  (h) β (beta) recombinase;
  (i) R recombinase;
  (j) γδ (gamma delta) resolvase;
  (k) Dre recombinase;
  (l) phi Rv1 integrase;
  (m) Int;
  (n) IHF;
  (o) Xis;
  (p) Fis;
  (q) Hin;
  (r) Gin;

(s) Cin;
(t) Th3 resolvase;
(u) TndX;
(v) XerC; and
(w) XerD.

3. The system according to claim 1, wherein said recombination sequence comprises one or more recombination sequences selected from the group consisting of:
(a) loxP;
(b) frt;
(c) attB/attP;
(d) six;
(e) RS;
(f) res;
(g) rox;
(h) psi;
(i) dif;
(j) cer; and
(k) mutants, variants, and derivatives of the recombination sequence from (a), (b), (c), (d), (e), (f), (g), (h), (i) or (j), which have retained the capability of provoking recombination.

4. The system according to claim 1, wherein said recombination enzyme is Cre recombinase and said recombination sequence is the loxP sequence.

5. The system according to claim 1, wherein said target gene is a transcription factor.

6. A gene expression control method for controlling the expression of a target gene inside a cell in vitro or in a non-human transgenic animal by the presence or absence of a tetracycline antibiotic, comprising the step of expressing under the presence or under the absence of the antibiotic inside said cell,
(a) an expression vector comprising expressibly
(a1) a polynucleotide encoding a fusion protein of a mutant of a tetracycline repressor protein and a recombination enzyme, wherein said fusion protein mediates the recombination at a recombination sequence site, and is degraded inside said cell in the absence of said antibiotic,
wherein said mutant has an amino acid sequence having at least two of the following mutations: substitution of aspartic acid at position 95 with asparagine, substitution of leucine at position 101 with serine and substitution of glycine at 102 with aspartic acid in the amino acid sequence of a wild-type tetracycline repressor protein encoded by SEQ ID NO: 2, and
(a2) a polynucleotide encoding a protein that binds to the transcription control region of the polynucleotide in (a1) and controls the transcription of said polynucleotide, wherein the binding to said transcription control region is controlled by the presence or absence of said antibiotic, and
(b) an expression vector comprising expressibly a target gene between and/or downstream of recombination sequences.

7. The method according to claim 6, wherein said recombination enzyme is at least one protein selected from the group consisting of:
(a) Cre recombinase;
(b) FLP recombinase;
(c) phage phi 13 integrase;
(d) phage R4 integrase;
(e) phage TP901-1 integrase;
(f) phage λ (lambda) integrase;
(g) phage HK022 integrase;
(h) β (beta) recombinase;
(i) R recombinase;
(j) γδ (gamma delta) resolvase;
(k) Dre recombinase;
(l) phi Rv1 integrase
(m) Int;
(n) IHF;
(o) Xis;
(p) Fis;
(q) Hin;
(r) Gin;
(s) Cin;
(t) Th3 resolvase;
(u) TndX;
(v) XerC; and
(w) XerD.

8. The method according to claim 6, wherein said recombination sequence comprises one or more recombination sequences selected from the group consisting of:
(a) loxP;
(b) frt;
(c) attB/attP;
(d) six;
(e) RS;
(f) res;
(g) rox;
(h) psi;
(i) dif;
(j) cer; and
(k) mutants, variants, and derivatives of the recombination sequence from (a), (b), (c), (d), (e), (f), (g), (h), (i) or (j), which have retained the capability of provoking recombination.

9. The method according to claim 6, wherein said recombination enzyme is Cre recombinase and the recombination sequence is the loxP sequence.

10. The method according to claim 6, wherein said target gene is a transcription factor.

11. The system according to claim 1, wherein said expression vector in (b) comprises a polynucleotide encoding a polypeptide comprising a nuclear export sequence added to the C-terminal side of the amino acid sequence of the fusion protein in (b1).

12. The system according to claim 5, wherein said transcription factor is any of Oct3/4, Klf4, Sox2, or c-Myc gene.

13. The method according to claim 6, wherein said expression vector in (a) comprises a polynucleotide encoding a polypeptide comprising a nuclear export sequence added to the C-terminal side of the amino acid sequence of the fusion protein in (a1).

14. A gene expression control system for controlling the expression of a target gene inside a cell in vitro or in a non-human transgenic animal by the presence or absence of a tetracycline antibiotic, comprising
(a) cell
(b) an expression vector that is introduced into the interior of said cell, and comprises expressibly a polynucleotide encoding a fusion protein of a mutant of a tetracycline repressor protein and a recombination enzyme, wherein said fusion protein mediates the recombination at the recombination sequence site, and is degraded inside said cell in the absence of said antibiotic,
wherein said mutant has an amino acid sequence having at least two of the following mutations: substitution of aspartic acid at position 95 with asparagine, substitution of leucine at position 101 with serine and substitution of glycine at 102 with aspartic acid in the amino acid sequence of a wild-type tetracycline repressor protein encoded by SEQ ID NO: 2,
(c) an expression vector that is introduced into the interior of said cell, and comprises expressibly a polynucleotide encoding a protein that binds to the transcription control region of the polynucleotide in (b) and controls the transcription of said polynucleotide, wherein the binding to said transcription control region is controlled by the presence or absence of said antibiotic,
(d) an expression vector that is introduced into the interior of said cell, and comprises expressibly a target gene between and/or downstream of recombination sequences, and
(e) said antibiotic to be introduced into the interior of said cell,
wherein the transcription of the polynucleotide in (b) and the degradation of the fusion protein, which is the expression product of the polynucleotide in (b), is controlled inside said cell by the presence or absence of the antibiotic, and the expression of the target gene is controlled by the expressed amount of the fusion protein.

15. A gene expression control method for controlling the expression of a target gene inside a cell in vitro or in a non-human transgenic animal by the presence or absence of a tetracycline antibiotic, comprising the step of expressing, in the presence or under the absence of the antibiotic inside said cell, (a) an expression vector comprising expressibly a polynucleotide encoding a fusion protein of a mutant of a tetracycline repressor protein and a recombination enzyme, wherein said fusion protein mediates the recombination at the recombination sequence site, and is degraded inside said cell in the absence of said antibiotic,
wherein said mutant has an amino acid sequence having at least two of the following mutations: substitution of aspartic acid at position 95 with asparagine, substitution of leucine at position 101 with serine and substitution of glycine at 102 with aspartic acid in the amino acid sequence of a wild-type tetracycline repressor protein encoded by SEQ ID NO: 2,
(b) an expression vector comprising expressibly a polynucleotide encoding a protein that binds to the transcription control region of the polynucleotide in (a) and controls the transcription of said polynucleotide, wherein the binding to said transcription control region is controlled by the presence or absence of said antibiotic, and
(c) an expression vector comprising expressibly a target gene between and/or downstream of recombination sequences.

* * * * *